(12) United States Patent
Raichman

(10) Patent No.: US 11,717,028 B2
(45) Date of Patent: Aug. 8, 2023

(54) VAPORIZING DEVICES AND METHODS FOR DELIVERING A COMPOUND USING THE SAME

(71) Applicant: Altria Client Services LLC, Richmond, VA (US)

(72) Inventor: Yossef Raichman, Herzliya (IL)

(73) Assignee: Altria Client Services LLC, Richmond, VA (US)

( * ) Notice: Subject to any disclaimer, the term of this patent is extended or adjusted under 35 U.S.C. 154(b) by 578 days.

(21) Appl. No.: 16/916,573

(22) Filed: Jun. 30, 2020

(65) Prior Publication Data
US 2021/0015153 A1 Jan. 21, 2021

Related U.S. Application Data

(63) Continuation of application No. 15/845,501, filed on Dec. 18, 2017, now Pat. No. 10,721,967, which is a
(Continued)

(51) Int. Cl.
*A24F 40/42* (2020.01)
*A24F 40/40* (2020.01)
(Continued)

(52) U.S. Cl.
CPC .............. *A24F 40/42* (2020.01); *A24F 40/40* (2020.01); *A24F 40/46* (2020.01); *A24F 40/50* (2020.01);
(Continued)

(58) Field of Classification Search
None
See application file for complete search history.

(56) References Cited

U.S. PATENT DOCUMENTS 6,040,560 A * 3/2000 Fleischhauer .......... A61M 11/04
219/494
8,897,628 B2 11/2014 Conley et al.
(Continued)

FOREIGN PATENT DOCUMENTS

CN 103932406 A 7/2014
EP 2399636 A1 12/2011
(Continued)

OTHER PUBLICATIONS

Office Action dated Aug. 9, 2022, issued in corresponding U.S. Appl. No. 16/801,780.
(Continued)

*Primary Examiner* — Michael J Felton
(74) *Attorney, Agent, or Firm* — Harness, Dickey & Pierce, P.L.C.

(57) ABSTRACT

A method of treating disorders in a human or animal subject may include heating a material containing a compound to a first temperature to form a heated volume of the material. The method may additionally include heating the heated volume to a higher second temperature to form a dose of vapor including the compound. The method may also include administering the dose of vapor to the subject to treat disorders such as pain. The method may further include pre-heating the material to a preliminary temperature prior to the heating to the first temperature. The heating and pre-heating may be performed with a capsule including two covering layers, each including an electrically conductive material, configured to hold the material therebetween and to generate heat by resistive heating.

13 Claims, 15 Drawing Sheets

Related U.S. Application Data continuation-in-part of application No. PCT/IL2017/051041, filed on Sep. 14, 2017.

(60) Provisional application No. 62/525,773, filed on Jun. 28, 2017, provisional application No. 62/500,509, filed on May 3, 2017, provisional application No. 62/453,544, filed on Feb. 2, 2017, provisional application No. 62/394,243, filed on Sep. 14, 2016.

(51) Int. Cl.
| | |
|---|---|
| *A24F 40/46* | (2020.01) |
| *A24F 40/57* | (2020.01) |
| *A24F 40/50* | (2020.01) |
| *A61M 11/04* | (2006.01) |
| *A61M 15/00* | (2006.01) |
| *A61P 25/36* | (2006.01) |
| *A61P 27/06* | (2006.01) |
| *A61P 25/30* | (2006.01) |
| *A61P 43/00* | (2006.01) |
| *A61P 11/06* | (2006.01) |
| *A61P 25/18* | (2006.01) |
| *A61P 25/08* | (2006.01) |
| *A61P 29/00* | (2006.01) |
| *A61P 1/08* | (2006.01) |
| *A61K 9/00* | (2006.01) |
| *A61K 31/05* | (2006.01) |
| *A61K 31/352* | (2006.01) |
| *A61K 36/185* | (2006.01) |
| *A61M 15/06* | (2006.01) |
| *A24F 40/20* | (2020.01) |
| *A24F 40/60* | (2020.01) |
| *A24F 40/95* | (2020.01) |
| *A61M 16/00* | (2006.01) |

(52) U.S. Cl.
CPC .............. *A24F 40/57* (2020.01); *A61K 9/007* (2013.01); *A61K 31/05* (2013.01); *A61K 31/352* (2013.01); *A61K 36/185* (2013.01); *A61M 11/042* (2014.02); *A61M 15/00* (2013.01); *A61M 15/003* (2014.02); *A61M 15/06* (2013.01); *A61P 1/08* (2018.01); *A61P 11/06* (2018.01); *A61P 25/08* (2018.01); *A61P 25/18* (2018.01); *A61P 25/30* (2018.01); *A61P 25/36* (2018.01); *A61P 27/06* (2018.01); *A61P 29/00* (2018.01); *A61P 43/00* (2018.01); *A24F 40/20* (2020.01); *A24F 40/60* (2020.01); *A24F 40/95* (2020.01); *A61M 15/002* (2014.02); *A61M 15/0021* (2014.02); *A61M 2016/0024* (2013.01); *A61M 2205/3334* (2013.01); *A61M 2205/3368* (2013.01); *A61M 2205/8206* (2013.01)

(56) References Cited

U.S. PATENT DOCUMENTS

| | | |
|---|---|---|
| 2002/0092521 A1 | 7/2002 | Sullivan et al. |
| 2009/0301471 A1 | 12/2009 | Stirzel |
| 2009/0302019 A1* | 12/2009 | Selenski ................. A24F 40/50 219/482 |
| 2012/0046352 A1 | 2/2012 | Hospodor |
| 2013/0081623 A1 | 4/2013 | Buchberger |
| 2013/0298905 A1 | 11/2013 | Levin et al. |
| 2014/0299141 A1 | 10/2014 | Flick |
| 2014/0366898 A1 | 12/2014 | Monsees et al. |
| 2014/0373857 A1 | 12/2014 | Steinberg |
| 2015/0105455 A1 | 4/2015 | Bjorncrantz |
| 2015/0128976 A1 | 5/2015 | Verleur et al. |
| 2015/0136158 A1 | 5/2015 | Stevens et al. |
| 2015/0216237 A1 | 8/2015 | Wensley et al. |
| 2015/0223292 A1 | 8/2015 | Duffield et al. |
| 2015/0305410 A1 | 10/2015 | Liu |
| 2016/0021930 A1 | 1/2016 | Minskoff et al. |
| 2016/0150825 A1 | 6/2016 | Mironov et al. |
| 2016/0219938 A1 | 8/2016 | Mamoun et al. |
| 2016/0271347 A1 | 9/2016 | Raichman |
| 2016/0310684 A1 | 10/2016 | McCullough |
| 2016/0331913 A1 | 11/2016 | Bourque |
| 2016/0338407 A1 | 11/2016 | Kerdemelidis |
| 2017/0095624 A1 | 4/2017 | Davidson et al. |
| 2017/0127727 A1 | 5/2017 | Davidson et al. |
| 2017/0273357 A1 | 9/2017 | Barbuck |

FOREIGN PATENT DOCUMENTS

| | | |
|---|---|---|
| EP | 3160552 A1 | 5/2017 |
| WO | WO-2011/033396 A2 | 3/2011 |
| WO | WO-2013/060781 A1 | 5/2013 |
| WO | WO-2014/040988 A2 | 3/2014 |
| WO | WO-2014/139611 A1 | 9/2014 |
| WO | WO-2015/117704 A1 | 8/2015 |
| WO | WO-2016/001923 A2 | 1/2016 |
| WO | WO-2016/001925 A1 | 1/2016 |
| WO | WO-2016/005602 A1 | 1/2016 |
| WO | WO-2016/096927 A1 | 6/2016 |
| WO | WO-2016/147188 A1 | 9/2016 |

OTHER PUBLICATIONS

Advisory Action dated Mar. 3, 2023, issued in corresponding U.S. Appl. No. 16/333,446.
Office Action dated Jul. 18, 2022, issued in corresponding U.S. Appl. No. 16/333,446.
Office Action dated Nov. 6, 2022 issued in related Israeli Patent Application No. 271521.
International Search Report and Written Opinion for corresponding PCT/IL2017/051041 application dated Dec. 21, 2017.
International Search Report and Written Opinion for corresponding Application No. PCT/US18/38156 dated Aug. 30, 2018.
Final Office Action dated Sep. 24, 2019 in U.S. Appl. No. 15/845,501.
International Preliminary Report on Patentability Chapter I dated Dec. 31, 2019 in International Application No. PCT/US2018/038156.
International Preliminary Report on Patentability Chapter I dated Mar. 19, 2019 in International Application No. PCT/IL2017/051041.
Non-Final Office Action dated Feb. 19, 2019 in U.S. Appl. No. 15/845,501.
Notice of Allowance dated Mar. 31, 2020 in U.S. Appl. No. 15/845,501.
Extended European Search Report dated Apr. 17, 2020 for correspondinng European Application No. 17850419.7.
T. Veress et al., 'Determination of cannabinoid acids by high-performance liquid chromatography of their neutral derivatives formed by thermal decarboxylation' *Journal of Chromatography*, vol. 520, 1990, pp. 339-347.
Franz E. Dussy et al., 'Isolation of $\Delta^9$-THCA-A from hemp and analytical aspects concerning the determination of $\Delta^9$-THC in cannabis products' *Forensic Science International*, vol. 149, 2005, pp. 3-10.
European Office Action dated May 3, 2021, issued in corresponding European Application No. 17850419.7.
Office Action dated Dec. 27, 2022, issued in corresponding U.S. Appl. No. 16/333,446.
Office Action for Japanese Application No. 2019-572088 dated Mar. 8, 2022 and English translation.
Notice of Allowance dated Nov. 30, 2022, issued in corresponding U.S. Appl. No. 16/801,780.
Notice of Allowance dated Nov. 30, 2022, issued in corresponding U.S. Appl. No. 16/801,898.
Extended Search Report for European Application No. 18823783.8 dated Apr. 1, 2021.

(56) References Cited

OTHER PUBLICATIONS

Examination Report dated Jul. 14, 2022, issued in corresponding Australian Patent Application No. 2017328499.
Notice of Allowance dated Mar. 8, 2023 issued in related U.S. Appl. No. 16/801,898.
Notice of Allowance dated Mar. 16, 2023 issued in related U.S. Appl. No. 16/801,898.
Notice of Allowance dated Mar. 20, 2023, issued in related U.S. Appl. No. 16/801,780.
Office Action dated Mar. 21, 2023, issued in related U.S. Appl. No. 16/333,446.

* cited by examiner

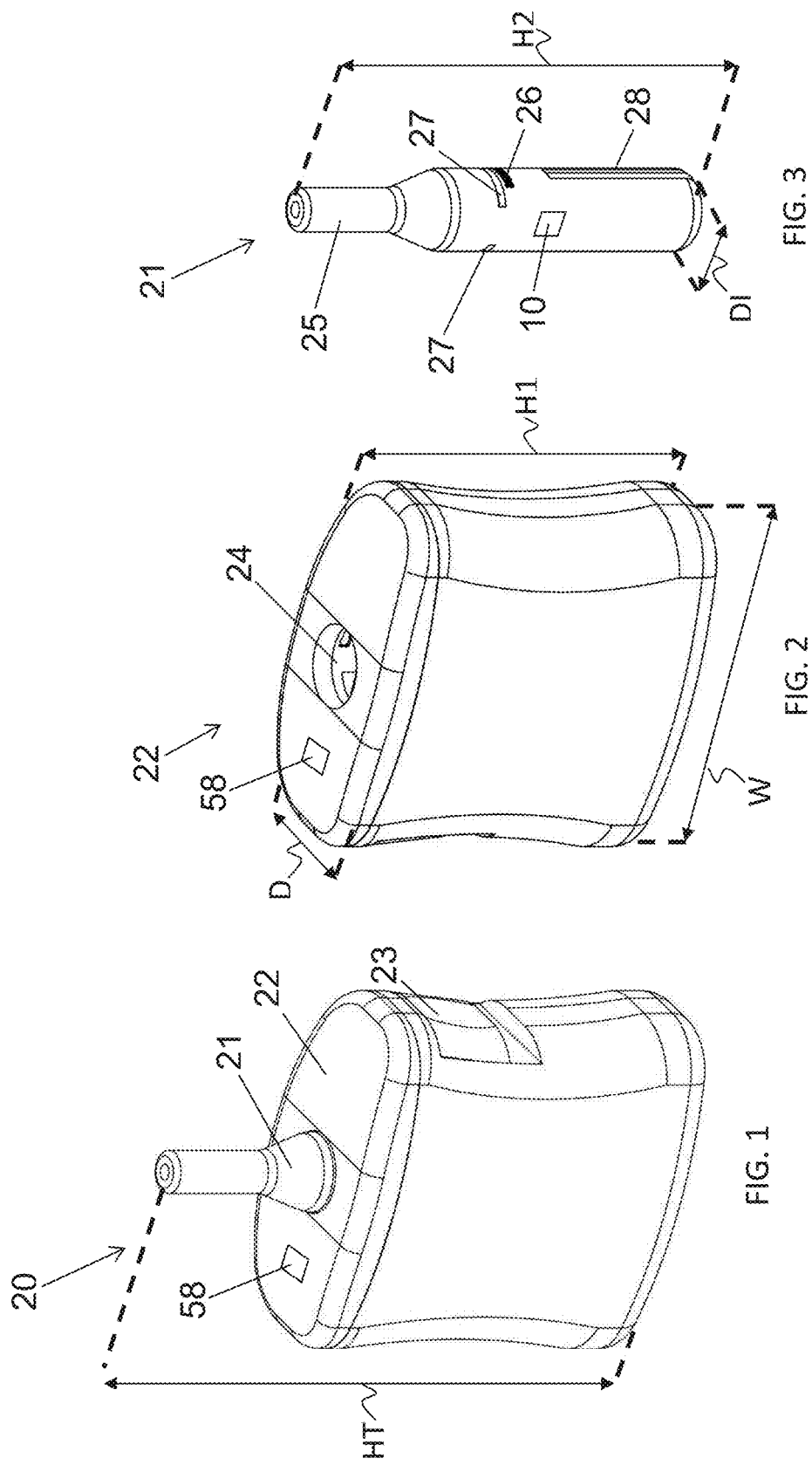

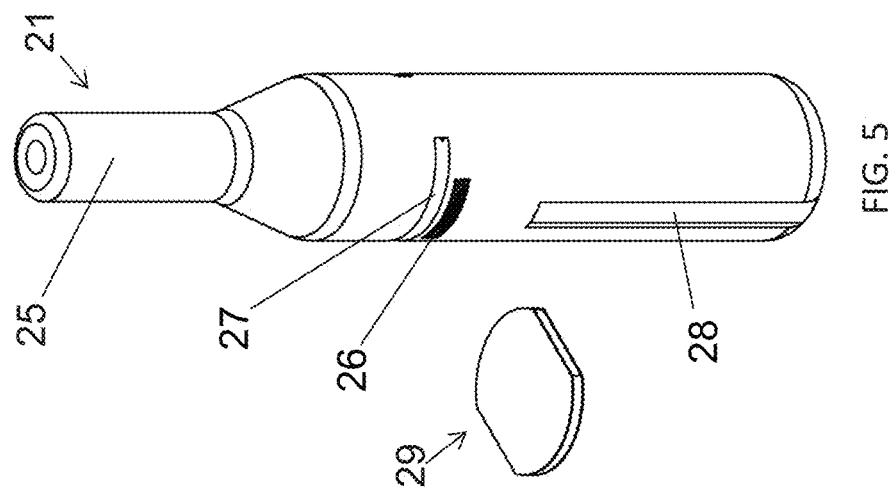
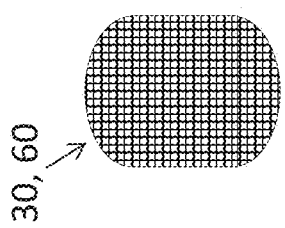
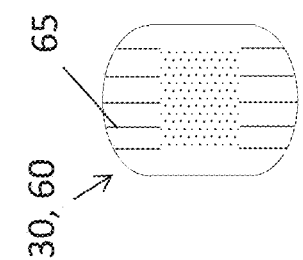
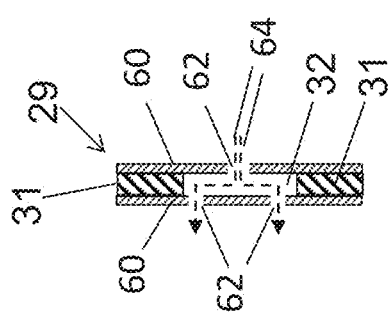
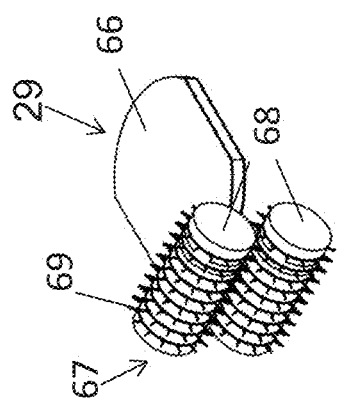
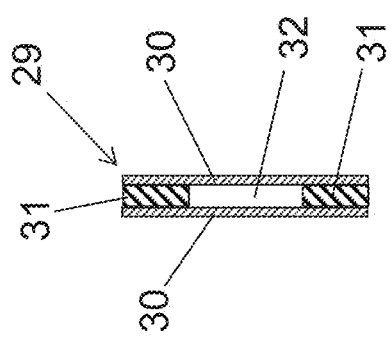
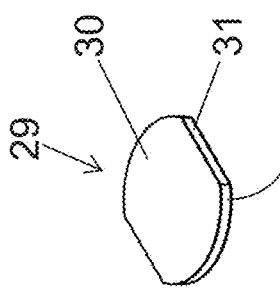

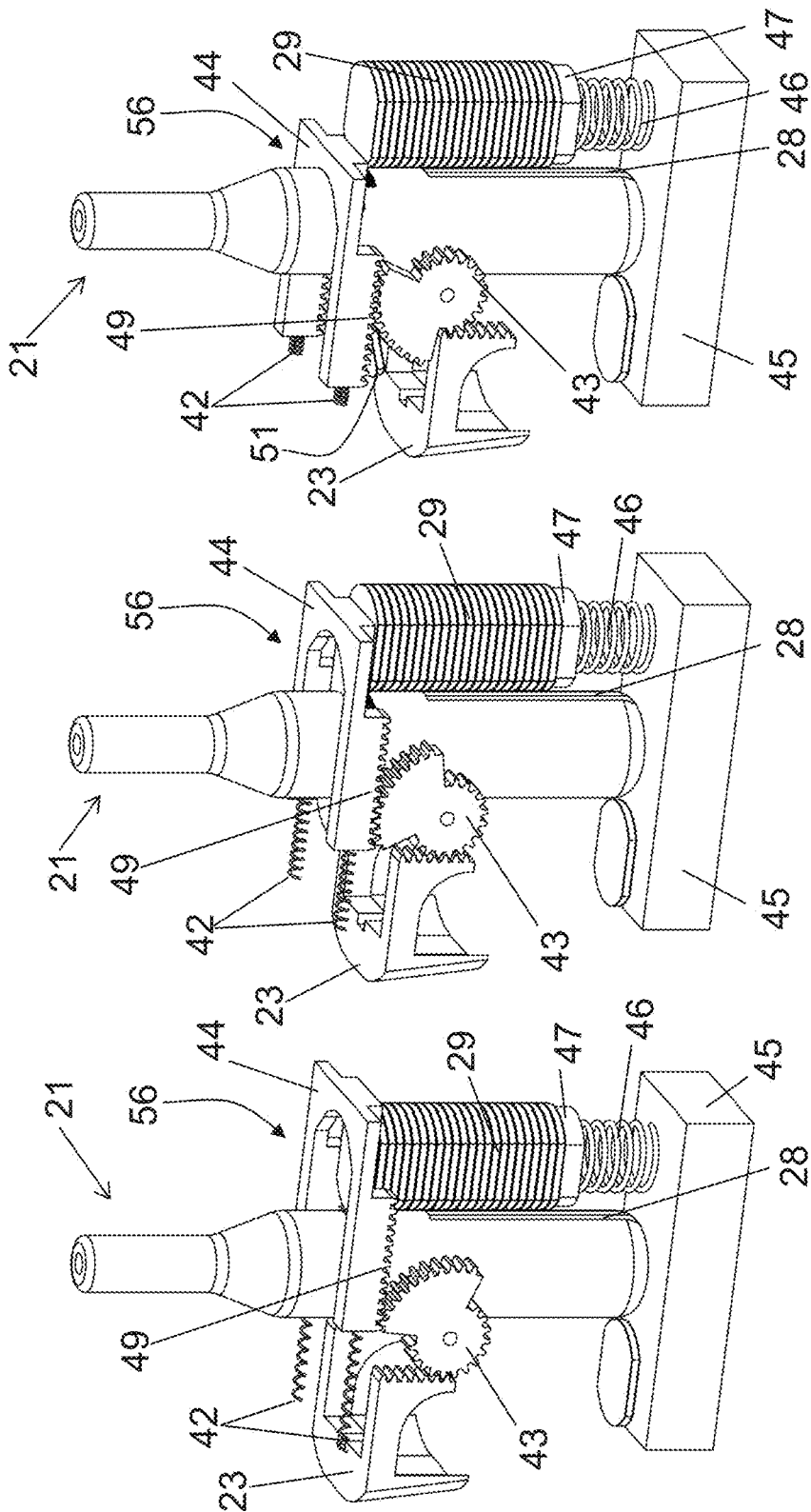

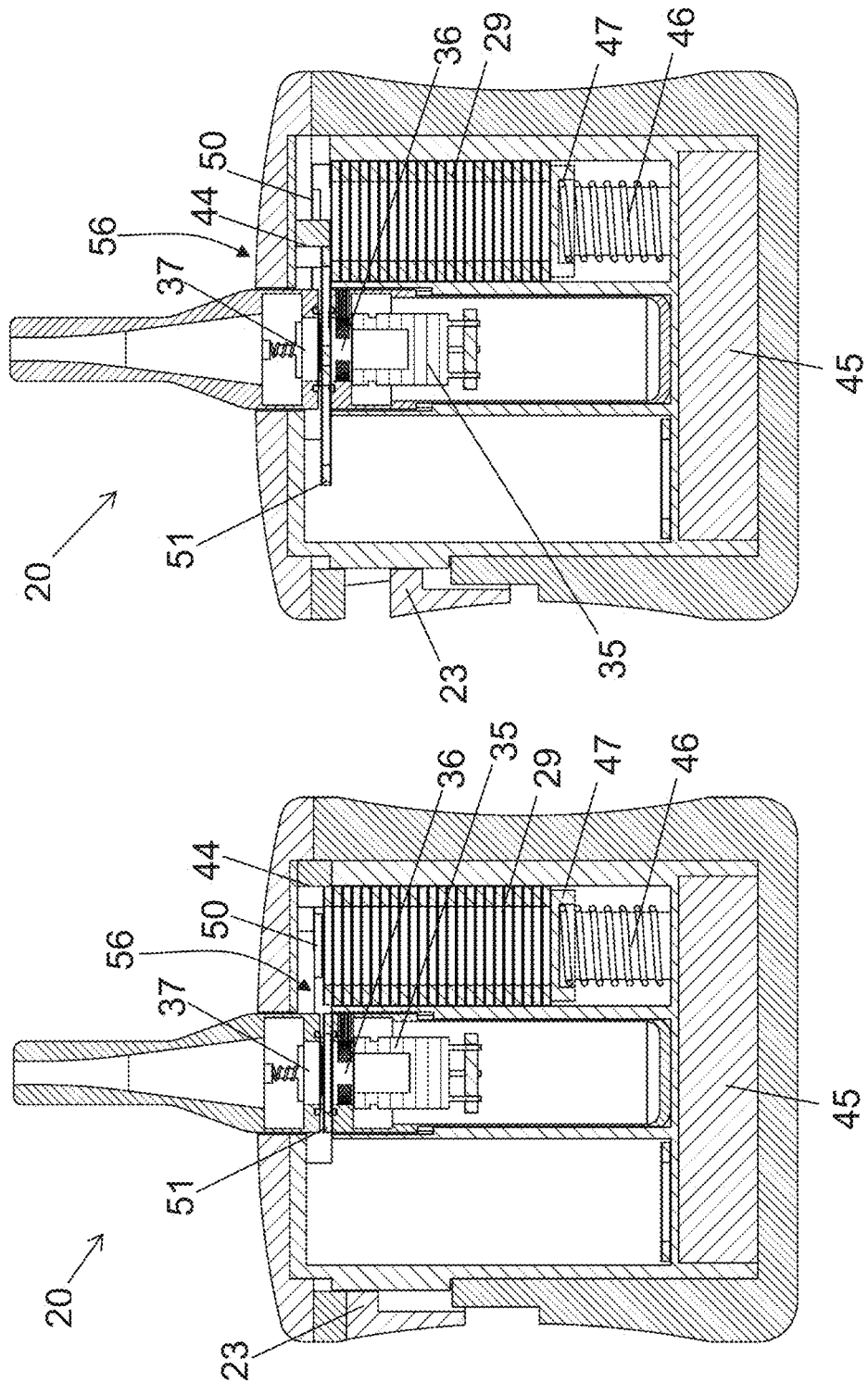

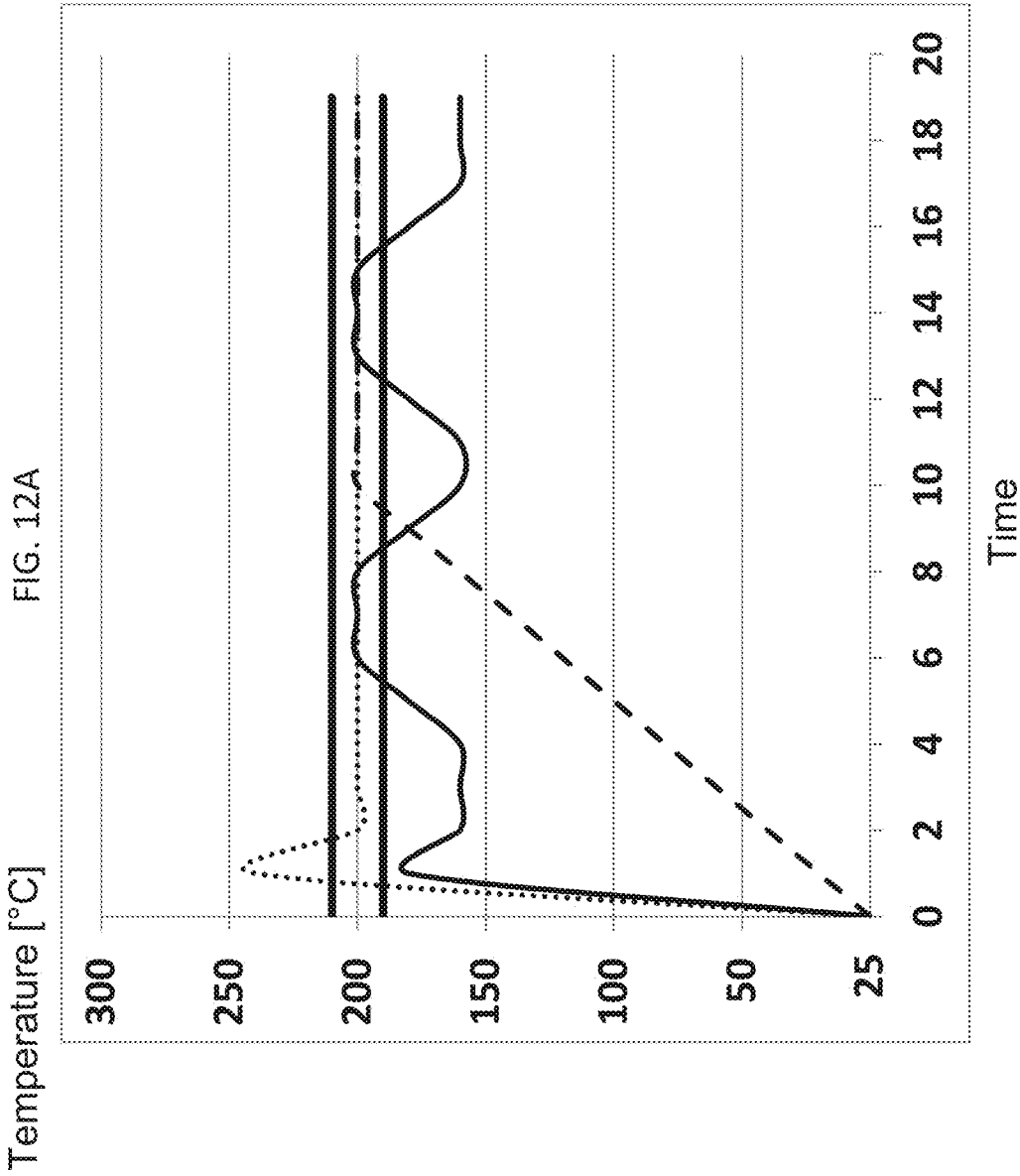

VAPORIZING DEVICES AND METHODS FOR DELIVERING A COMPOUND USING THE SAME

CROSS-REFERENCE TO RELATED APPLICATIONS

The present application is a continuation of U.S. application Ser. No. 15/845,501, filed Dec. 18, 2017, which is a continuation-in-part of International Application No. PCT/IL2017/051041, filed Sep. 14, 2017, which claims priority to U.S. Provisional No. 62/525,773, filed Jun. 28, 2017; U.S. Provisional No. 62/500,509, filed May 3, 2017; U.S. Provisional No. 62/453,544, filed Feb. 2, 2017; and U.S. Provisional No. 62/394,243, filed Sep. 14, 2016, the entire contents of each of which are incorporated herein by reference.

BACKGROUND

Field

Example applications herein generally relate to a vaporizing apparatus and methods of use. Specifically, some example applications relate to vaporizing devices and methods for the delivery of a compound to a subject.

Description of Related Art

The medical use of *cannabis* and its constituent cannabinoids, such as tetrahydrocannabinol (THC) and cannabidiol (CBD), includes the treatment of patients suffering from nausea, pain, muscle spasticity, and/or appetite loss. Medicinal *cannabis* can be administered using a variety of methods, including vaporizing or smoking the dried buds of the *cannabis* plant.

SUMMARY

The present technology provides methods for treating disorders in a human or animal subject, comprising administering to the subject a vapor produced in a device as described herein. In some applications, methods of treating disorders in a human or animal subject comprise heating a volume of THC/THCA-containing *cannabis* to a first temperature of 140° to 160° C. for 5 to 15 seconds to form a heated volume of the *cannabis*. The method may additionally comprise heating the heated volume of the *cannabis* to a second temperature of 190° to 200° C. for 2 to 5 seconds to form a dose of vapor comprising tetrahydrocannabinol (THC). The method may also comprise administering the dose of vapor to the subject. For instance, the dose of vapor may be administered to a human subject to treat disorders such as pain (e.g., postoperative pain). The method may further comprise pre-heating the volume of *cannabis* to a temperature of 90° to 110° C. for 5 to 15 seconds prior to the heating to the first temperature.

The heating to the first temperature and the heating to the second temperature may be performed in a device comprising a capsule including two covering layers. The two covering layers, each including an electrically conductive material, are configured to hold the volume of *cannabis* therebetween and to generate heat by resistive heating. The device may further comprise a vaporizing unit configured to receive the capsule.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 1 is a perspective view of a vaporizing device, in accordance with an example embodiment;

FIG. 2 is a perspective view of a reloading unit of the vaporizing device of FIG. 1, in accordance with an example embodiment;

FIG. 3 is a perspective view of a vaporizing unit of the vaporizing device of FIG. 1, in accordance with an example embodiment;

FIG. 4A is a perspective view of a capsule configured to contain a material, in accordance with an example embodiment;

FIG. 4B is a cross-sectional view of the capsule of FIG. 4A, in accordance with an example embodiment;

FIG. 4C is a cross-sectional view of a capsule including perforated sheets, in accordance with an example embodiment;

FIG. 4D is a plan view of a mesh of a capsule, in accordance with an example embodiment;

FIG. 4E is a plan view a perforated sheet of a capsule, in accordance with an example embodiment;

FIG. 4F is a perspective view of a capsule including non-perforated sheets and a perforating mechanism configured to puncture the sheets of the capsule, in accordance with an example embodiment;

FIG. 5 is a perspective view of a vaporizing unit and a capsule aligned for insertion into the vaporizing unit, in accordance with an example embodiment;

FIGS. 8A, 8B, and 8C are perspective views of internal components of a reloading unit with a vaporizing unit disposed therein, at respective stages of an operation of a capsule-loading mechanism, in accordance with an example embodiment;

FIGS. 9A, 9B, and 9C are cross-sectional views of a vaporizing device that includes a vaporizing unit placed in a reloading unit, at respective stages of an operation of a capsule-loading mechanism, in accordance with an example embodiment;

FIG. 12A is a graph illustrating a two-stage technique for heating a material using a vaporizer, in accordance with an example embodiment;

DETAILED DESCRIPTION

Figure 7:
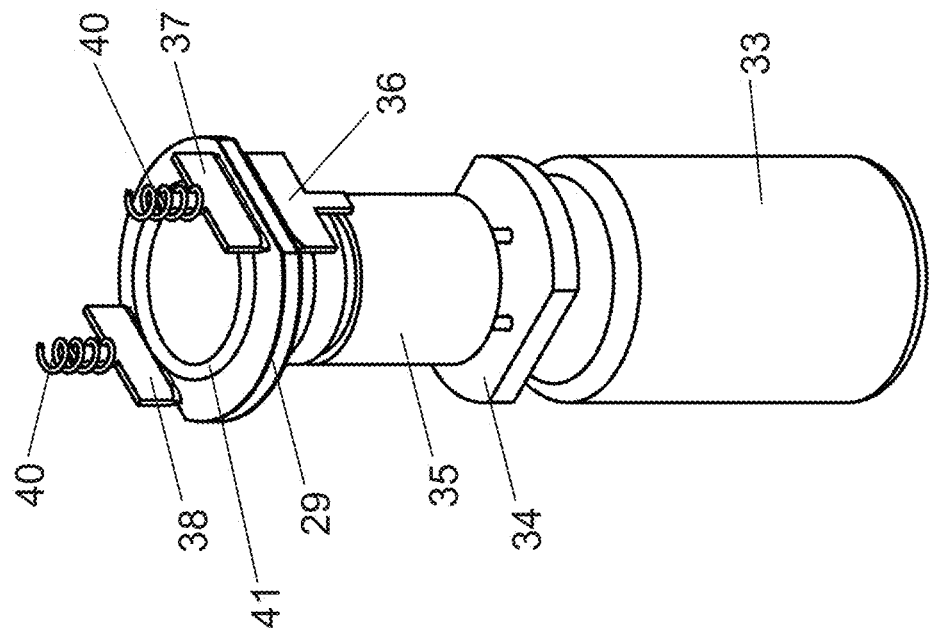
FIG. 7 is a perspective view of internal components of the vaporizing unit of FIG. 3 with a capsule disposed at a vaporization location within the vaporizing unit, in accordance with an example embodiment.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

In the following description, illustrative embodiments may be described with reference to acts and symbolic representations of operations (e.g., in the form of flow charts, flow diagrams, data flow diagrams, structure diagrams, block diagrams, etc.) that may be implemented as program modules or functional processes including routines, programs, objects, components, data structures, etc., that perform particular tasks or implement particular abstract data types. The operations be implemented using existing hardware in existing electronic systems, such as one or more microprocessors, Central Processing Units (CPUs), digital signal processors (DSPs), application-specific-integrated-circuits (ASICs), SoCs, field programmable gate arrays (FPGAs), computers, or the like.

One or more example embodiments may be (or include) hardware, firmware, hardware executing software, or any combination thereof referred to as control circuitry. Such hardware may include one or more microprocessors, CPUs, SoCs, DSPs, ASICs, FPGAs, computers, or the like, configured as special purpose machines to perform the functions described herein as well as any other well-known functions of these elements. In at least some cases, CPUs, SoCs, DSPs, ASICs and FPGAs may generally be referred to as processing circuits, processors and/or microprocessors.

Although processes may be described with regard to sequential operations, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

FIG. 1 is a perspective view of a vaporizing device 20, which includes a reloading unit 22 and a vaporizing unit 21, in accordance with an example embodiment. The reloading unit 22 and the vaporizing unit 21 are shown separately in FIG. 2 and FIG. 3, respectively. The vaporizing device 20 may be used to vaporize a compound within or of a material, such as plant material. As referred to herein, a compound includes one or more compounds that are to be vaporized during a method of the present technology, such as one or more compounds that have specific physiological or sensory effects when inhaled, consumed, or otherwise taken in by a subject. For example, the subject may be a patient in need of medical treatment, as discussed further below.

The vaporizing device 20 may be used to vaporize one or more compounds (e.g., the constituent cannabinoids) of *cannabis* (e.g., tetrahydrocannabinol (THC) and/or cannabidiol (CBD)). Alternatively or additionally, the vaporizer may be used to vaporize a compound from tobacco (e.g., naturally-occurring constituent such as nicotine), and/or other plant or chemical substances that contain a compound that becomes vaporized upon heating. It is noted that some applications are described with reference to a plant material that contains one or more compounds that become vaporized upon heating. However, the scope of the present disclosure includes using any substance that contains a compound suitable for vaporization (e.g., a synthetic substance that contains one or more compounds), mutatis mutandis. The vaporizing device 20 may alternatively be referred to as an "electronic vaping device," and in the context of the present application, these terms should be interpreted as being interchangeable with one another. Similarly, in the context of the present application, the terms "vaporizing unit," "vaporizer," and "electronic vaping device" should be interpreted as being interchangeable with one another.

For some applications, the vaporizing device 20 includes a reloading unit 22 and a vaporizing unit 21. For some applications, the reloading unit houses capsules 29, a capsule-loading mechanism 56, and a power supply 45, as described in further detail herein below. For some applications, the vaporizing unit houses a vaporization location 54, a power supply 33 (e.g., an internal power supply), and control circuitry 34. The control circuitry is configured to act as a control unit or controller, which controls the functioning of the vaporizing unit. The reloading unit and the vaporizing unit may be reversibly couplable to each other. The vaporizing device is configured, such that in order to load a capsule into the vaporizing unit, and/or to discard a used capsule from the vaporizing unit, the vaporizing unit is coupled to the reloading unit, before activating the capsule-reloading mechanism, as described in further detail hereinbelow. Subsequently, in order to vape from the vaporizing unit, the vaporizing unit may be detached from the reloading unit if desired. The vaporizing unit 21 may include a mouthpiece 25. During the operation of the vaporizing unit 21, the vaporizing unit 21 may vaporize one or more compounds of the plant material that is disposed inside a capsule 29, by heating the capsule 29, while the capsule 29 is disposed at the vaporization location 54. The vaporized compound is drawn from the vaporizing unit 21 via the mouthpiece 25.

The vaporizing device 20 may be configured to be portable such that, during use, the vaporizing unit 21 can be held with one hand. The dimensions of the vaporizing unit 21 may be as follows:

A height H1 of reloading unit 22 may be more than 5 cm (e.g., more than 6 cm), and/or less than 15 cm (e.g., less than 12 cm), e.g., between 5 cm and 15 cm, or between 10 and 12 cm.

A height H2 of vaporizing unit 21, may be more than 6 cm (e.g., more than 8.3 cm), and/or less than 12 cm (e.g., less than 10 cm), e.g., between 7 cm and 9 cm, or between 8 and 8.5 cm.

The total height HT of the vaporizing device 20, including the vaporizing unit 21 inserted into the reloading unit 22, may be less than 20 cm, e.g., less than 11 cm.

A width W of reloading unit 22 may be more than 4 cm (e.g., more than 6 cm), and/or less than 9 cm (e.g., less than 7), e.g., between 4 cm and 9 cm, or between 6 cm and 7 cm.

A depth D of reloading unit 22 may be more than 2 cm (e.g., more than 3 cm), and/or less than 6 cm (e.g., less than 4 cm), e.g., between 2 cm and 6 cm, or between 3 cm and 4 cm.

For applications in which vaporizing unit 21 has a circular cross-section (as shown in FIG. 3), a diameter DI of the vaporizing unit may be more than 5 mm (e.g., more than 6 mm), and/or less than 35 mm (e.g., less than 20 mm), e.g., between 5 mm and 35 mm, or between 6 mm and 20 mm. For applications in which the vaporizing unit has a non-circular cross-section, the cross-sectional area of the vaporizing unit may be the equivalent of a circle having a diameter as described in the previous sentence.

For some applications, a capsule-loading button 23 is disposed on the outside of reloading unit 22. The capsule-loading button controls capsule-loading mechanism 56 (FIGS. 8A-C). As described in further detail hereinbelow, the capsule-loading mechanism is configured to (a) individually transfer unused capsules from a first receptacle 53 (FIG. 9C) within the body of the reloading unit to a vaporization location 54 (FIG. 6) within the body of vaporizing unit 21, at which the capsule is heated such as to vaporize the compound, and (b) to individually transfer used capsules from the vaporization location within the vaporizing unit to a second receptacle 52 (FIG. 9C) within the body of the reloading unit. Alternatively or additionally, capsule-loading mechanism 56 (or any other capsule-loading mechanism described herein) is controlled by an electric motor (not shown).

Reference is now made to FIGS. 4A-B, which are perspective and cross-section views, respectively, of a capsule 29, configured to contain a material 32, e.g., a plant material that includes one or more compounds, in accordance with an example embodiment. As described hereinabove, for some applications, the plant material is *cannabis*, and the compounds are the constituent cannabinoids of *cannabis* (e.g., tetrahydrocannabinol (THC) and/or cannabidiol (CBD)). *Cannabis* plant material includes the leaf and/or flower material from one or more *cannabis* species such as *Cannabis sativa, Cannabis indica*, and *Cannabis ruderalis*. In some applications, *cannabis* plant material is obtained from *Cannabis sativa*, or combinations of *sativa* with other *cannabis* species. Alternatively or additionally, the plant material includes tobacco (and the compound includes nicotine), and/or other plant or chemical substances that contain a compound that becomes vaporized upon heating. The term "tobacco" includes any tobacco plant material including tobacco leaf, tobacco plug, reconstituted tobacco, compressed tobacco, shaped tobacco, or powder tobacco, and combinations thereof from one or more species of tobacco plants, such as *Nicotiana rustica* and *Nicotiana tabacum*.

The capsule 29 may be similar to the capsules described in WO 16/147188, the entire disclosure of which is incorporated herein by reference. For some applications, the material 32 (which contains one or more compounds, and which may be a plant material) is housed between covering layers, which may be upper and lower meshes (e.g., metallic meshes) 30. For some applications, each of the meshes has openings of more than 15 micron (e.g., more than 20 micron), and/or less than 80 micron (e.g., less than 50 micron), e.g., 15-60 micron, or 20-50 micron. The meshes 30 may be coupled to a central portion 31 of the capsule (e.g., a central disc, as shown), the central portion 31 defining a hole. For example, the central portion 31 may be formed of cellulose fibers (e.g. wood, hemp, tobacco), plastic (e.g., polyether ether ketone (PEEK)), or other suitable temperature-resistant insulator. In a non-limiting embodiment, the central portion 31 may be formed of cardboard. Additionally, the meshes 30 may be coupled to the central portion 31 via an adhesive, such as a high-temperature-resistant glue, or double-sided adhesive or ultrasonically welded to the central portion 31 or heat pressed onto the central portion 31. The adhesive may be configured so as to not emit fumes, even when the adhesive is subjected to a relatively high temperature, such as a temperature of greater than 200 degrees Celsius. The material 32 may be housed between the meshes 30 and within the hole defined by the central portion 31 of the capsule 29.

The material 32 (e.g., plant material) may be ground, such that (a) the material 32 is in sufficiently small pieces that the material 32 fits within the capsule 29, and a relatively large surface area of the material 32 is exposed to air flow through the vaporizing unit 21 (*b*) the pieces of the material 32 are sufficiently large that they do not pass through the meshes 30, and (c) the compound within the material 32 retains its potency. For some applications, the material 32 is cryogenically ground and/or powderized.

For some applications, central portion 31 of capsule 29 is made of a material that has a high heat capacity and/or low heat conductivity so that it reduces heat loss from the capsule to the surrounding area and reduces heating of the surrounding area during the vaporization process. For some applications, at least one of the wires of meshes 30 is hollow, and a phase-change material is disposed inside the hollow wire. Alternatively or additionally, a phase-change material is coupled to the capsule is a different manner, e.g., by coating the capsule with the phase-change material. For some applications, the phase-change material is configured to reduce heat loss from the capsule, by causing the capsule to absorb heat relative to the areas surrounding the capsule. Alternatively or additionally, the phase-change material is selected such as to maintain the capsule below the pyrolysis temperature of the plant material, and to thereby reduce or prevent the plant material from being pyrolyzed. For example, the phase-change material may undergo a phase-change at a temperature that is between the vaporization temperature and the pyrolysis temperature of the plant material, such that the phase-change material absorbs heat as latent heat of fusion at this temperature. For some applications, a phase-change material is coupled to the capsule in order to facilitate the automatic identification of the capsule type, by the control circuitry of the vaporizing unit, as described in further detail hereinbelow.

Reference is now made to FIG. 4C, which is a cross-section view of capsule 29 with perforated sheets 60, in accordance with an example embodiment. For some applications, the material 32 (e.g., plant material) is housed inside the central portion of the capsule between first and second perforated sheets. As shown in FIG. 4C, the upper and lower perforated sheets 60 may be used as covering layers for covering the material 32, instead of the upper and lower meshes 30 as shown in FIG. 4B, for example. For some applications, each of the perforated sheets 60 defines one or more perforations 62 that are configured to guide airflow through the material 32 along a given airflow path, during the vaporization process. For example, FIG. 4C shows airflow arrows 64, which illustrate an airflow path that is generated by perforations 62. The perforations 62 may be configured to guide airflow through the material 32 along an airflow path that increases contact area between the flowing air and the material 32 within the capsule 29. For some applications, the perforated sheets 60 are configured to be heated in a similar manner to that described herein with reference to meshes 30, mutatis mutandis. For example, the perforated sheets 60 may be made of an electrical conductive material that is configured to be heated via resistive heating. In general, techniques that are described herein with reference to the capsule 29 that includes meshes 30 as the covering layers for covering the material 32, may be performed with respect to the capsules 29 that include perforated sheets 60 as the covering layers for covering the material 32, mutatis mutandis.

Reference is now made to FIGS. 4D and 4E, which are plan views of a mesh 30 or a perforated sheet 60, respectively, in accordance with an example embodiment. For some applications, the perforation pattern of the perforated sheets 60, or the pattern of holes in the meshes 30, is uniform across the surface of each of the perforated sheets 60, or each of the meshes 30, as shown in FIG. 4D, for example. Alternatively, the perforation pattern of the perforated sheets, or the pattern of holes in the meshes, is non-uniform across the surface of each of the perforated sheets, or each of the meshes, as shown in FIG. 4E, for example. For some applications, the perforation pattern of the perforated sheets, or the pattern of holes in the meshes, is varied across the surface of each of the perforated sheets, or each of the meshes, in order to control the resistance and/or the resistivity pattern of the sheet. For example, use of selective perforation may be implemented in order to limit resistive heating to the contact area between the perforated sheet or the mesh and the plant material, and/or to focus the resistive heating upon that area. Alternatively or additionally, non-uniform perforation spacing may be used, for example, to control the current density at different locations across the surface of the perforated sheets, or the meshes. An example of this is shown in FIG. 4E, which shows slits 65 on mesh 30 or perforated sheet 60, the slit being configured to reduce or prevent electrical current from flowing across the mesh or the sheet at regions at which the plant material is not housed. As described hereinabove, for some applications, perforations 62 are disposed upon the sheets to form perforated sheets 60 such as to guide airflow through the plant material along a given airflow path, during the vaporization process.

Reference is now made to FIG. 4F, which is a perspective view of capsule 29 and a perforating mechanism 67, in accordance with an example embodiment. For some applications, capsule 29 is configured to be provided with a material 32 (e.g., plant material) within the capsule 29 covered by non-perforated sheets 66, the non-perforated sheets 66 acting as the covering layers for covering the material 32. For example, the capsules 29 may be provided in this state, such that the non-perforated sheets 66 preserve the material 32 within the capsule 29, and/or maintain the potency of the compound within the material 32. Prior to the material 32 being heated inside the vaporizer, the non-perforated sheets 66 may be punctured or pierced to form perforated sheets 60, in order to allow airflow through the capsule 29. For some applications, the sheets are perforated prior to placing the capsule inside the vaporizer. Alternatively, the vaporizer includes a perforating mechanism 67 that is configured to puncture or pierce the non-perforated sheets 66 to form perforated sheets 60 prior to the material 32 being heated inside the vaporizer. For example, as shown in FIG. 4F (which shows the perforating mechanism in the absence of the other components of the vaporizer, for illustrative purposes), the perforating mechanism may include one or more rollers 68 with pins 69 disposed thereon. For some applications, the perforation mechanism 67 is configured to puncture or pierce the non-perforated sheets 66 to form perforated sheets 60, such that the perforation pattern that is formed is uniform across the surface of each of the perforated sheets 60, for example, as shown in FIG. 4D. Alternatively, the perforation mechanism 67 is configured to puncture or pierce the non-perforated sheets 66 to form perforated sheets 60, such that the perforation pattern that is formed is non-uniform across the surface of each of the perforated sheets 60, for example, as shown in FIGS. 4C and 4E. For some applications, the non-perforated sheets 66 are configured to be heated in a similar manner to that described herein with reference to meshes 30, mutatis mutandis.

The sheets (e.g., perforated sheets 60, non-perforated sheets 66) may be made of an electrically conductive material (e.g., metal foil) that is configured to be heated via resistive heating. In some applications, a sheet consists of a conductive material. In some embodiments, the sheets comprise two or more layers, one of which comprises a conductive material. For example, the sheets may be in a form of a layer of a non-conductive material covered with a conductive material (e.g., metallic layer), which may be a pattern of metallic material deposited on the surface of the non-conductive material. Such non-conductive material may comprise cellulose fibers (e.g. wood, hemp, tobacco), plastic (e.g., polyether ether ketone (PEEK)). For example, the non-conductive material may be cellulosic paper or cardboard. In general, techniques that are described herein with reference to capsules 29 that include meshes 30 as the covering layers for covering the material 32 may be performed with respect to capsules 29 that include sheets that are perforated or non-perforated (and perforated prior to or during use) as the covering layers for covering the material 32, mutatis mutandis.

For some applications, capsule 29 is configured to keep the material 32 fully encapsulated prior to use. For example, such encapsulation may offer benefits such as minimizing contamination of the plant material, and preserving the plant materials to avoid degradation of plant material (e.g., minimizing a loss of one or more compounds prior to vaporization). For example, the capsule 29 may be configured in this manner by the use of non-perforated sheets 66, as described with reference to FIG. 4F.

Figure 6:
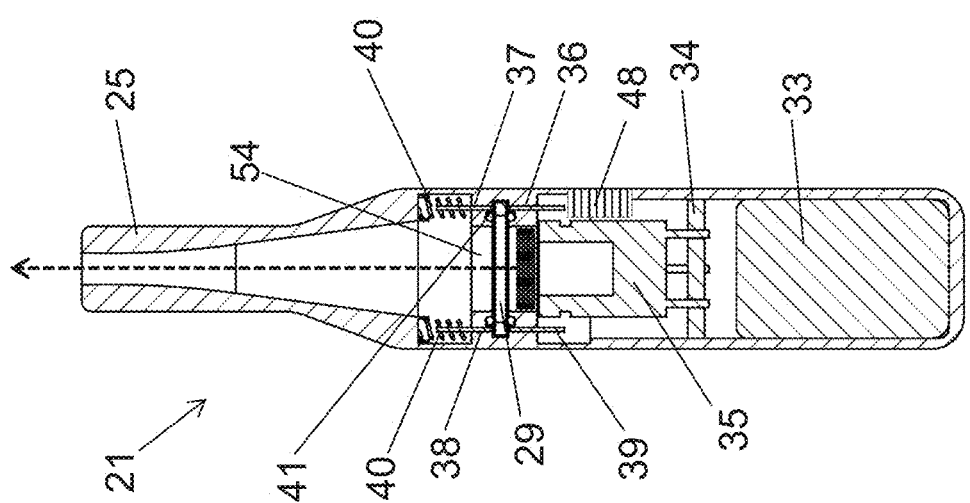
FIG. 6 is a cross-sectional view of the vaporizing unit of FIG. 3, in accordance with an example embodiment.

Reference is now made to FIGS. 5-7, which are various views of the vaporizing unit 21, in accordance with an example embodiment. For some applications, the vaporizing unit 21 receives capsules 29 by virtue of the vaporizing unit 21 being coupled to the reloading unit 22, and capsule-loading mechanism 56 is used to load capsules 29 into the vaporizing unit 21. Alternatively or additionally, the vaporizing unit 21 is used in the absence of the reloading unit 22. For example, individual capsules 29 may be inserted into the vaporizing unit 21. For some such applications, after the individual capsule has been depleted of the compound(s) therein, the individual capsule needs to be removed from the vaporizing unit before another capsule can be inserted. Alternatively, the vaporizing unit is configured such that a used capsule is automatically pushed out of the vaporization location, by a new capsule being inserted into the vaporization location. Furthermore, alternatively, the vaporizing unit is configured to hold a plurality of used capsules, such that the used capsules only need to be removed from the vaporizing unit periodically.

For some applications, the vaporizing unit of the vaporizing device is configured to be used with a plurality of different types of capsules. For example, respective types of capsules may contain different quantities of plant material, plant material containing different amount of compounds, and/or different types of plant materials. Alternatively or additionally, respective types of capsules may have respective characteristics, e.g., respective flavors, strengths, richness, etc. For some applications, the reloading unit is configured to allow the selection of which capsule type to place in the reloading unit, and the reloading unit may then be used to load the vaporizing unit with that type of capsule. Alternatively, a reloading unit may come preloaded with a given type of capsules. Furthermore, alternatively, as described hereinabove, the vaporizing unit may be configured such that the capsules can be inserted directly into the vaporizing unit. For such applications, a subject is able to select which type of capsule is desired at any given time for insertion into the vaporizing unit.

For some applications, control circuitry 34 of the vaporizing unit is configured to adjust a heating profile of the capsules to the capsule type that is currently being heated. For some such applications, the control circuitry implements an automatic capsule classification procedure in accordance with which the control circuitry automatically classifies the capsule that is currently being heated as a given type of capsule (i.e., the control circuitry identifies the capsule type), and designates a capsule heating profile accordingly.

For some applications, color coded capsules are used for identification of different capsules and/or for automatic classification of the capsule by the control circuitry of the vaporizing unit, for example, by use of a color sensor. In an example embodiment, the control circuitry includes a memory storing a color-to-profile lookup table (LUT). This LUT stores heating profiles in association with a corresponding color. The heating profiles for various capsules may be determined through empirical study. The association of a heating profile with a color may be a matter of design choice. Accordingly, when classifying a capsule by color, the control circuitry receives output from the color sensor indicating a color associated with the capsule, and accesses the corresponding heating profile from the LUT using the indicated color.

For some applications, the thermal emissivity of the capsules is used for classification of different capsules by the control circuitry, for example, by coating one or more of the metallic meshes of each of the capsules with coatings having respective thermal emissivity constants. For some applications, the identification of the above-mentioned thermal emissivity constant of the capsule is measured by the vaporizing unit, while the coating of the capsule is at a known temperature. For example, the control circuitry may measure the thermal emissivity of the capsule coating while the capsule is in an unused state, and can therefore be assumed to be approximately at ambient temperature. In an example embodiment, the control circuitry includes a memory storing an emissivity-to-profile lookup table (LUT). This LUT stores heating profiles in association with a corresponding thermal emissivity. The heating profiles for various capsules may be determined through empirical study. The association of a heating profile with a thermal emissivity may be a matter of design choice. Accordingly, when classifying a capsule by thermal emissivity, the control circuitry receives output from the temperature sensor indicating a thermal emissivity associated with the capsule, and accesses the corresponding heating profile from the LUT using the indicated thermal emissivity.

For some applications, a standard temperature sensor is used to measure thermal emissivity or the temperature of the capsule coating. For some applications, a temperature sensor as described hereinbelow is used to measure the temperature of the capsule coating.

For some applications, the control circuitry is configured to perform the classification of the capsule type by phase-change materials having respective phase-change temperatures being used with each capsule type. The phase-change material may be at least partially disposed within the capsules and is thermally coupled to one or more of the metallic meshes of the capsules. Furthermore, the phase-change temperature of the phase-change material may be below the vaporization temperature of the compound. During the heating of a capsule, the phase-change material reaches its phase-change temperature and accumulates latent heat, while it is in the process of undergoing the phase change. In accordance with respective applications, within the temperature range to which the capsule is heated, the phase-change material may be configured to undergo a phase change from solid to liquid, from liquid to gas, from gel to gas, and/or from solid to gas. While the phase-change material undergoes the phase change, the measured temperature of the phase-change material, and of the capsule, may remain relatively constant. The relatively constant temperature may be maintained for a short duration of time, followed by a continued increase in the temperature of the capsule after the phase change transition of the phase-change material has been completed. For some applications, the control circuitry is configured to detect the temperature at which the capsule's temperature remains constant for a given period of time, during the heating of the capsule. Since this temperature is indicative of the phase-change temperature, the control circuitry is configured to classify the capsule type in response to detecting this temperature. For example, different types of capsules can be classified by using phase-change materials with different phase-change temperatures. Purely by way of example, phase-change materials having phase-change temperature levels of approximately 60 degrees Celsius, approximately 65 degrees Celsius, approximately 70 degrees Celsius, approximately 75 degrees Celsius, and approximately 80 degrees Celsius can be used to classify five different types of capsules. As described hereinabove, in response to detecting a given capsule type, a capsule heating profile that is suited to that capsule type may be applied. In an example embodiment, the control circuitry includes a memory storing a LUT with temperature values of phase change materials in association with corresponding heating profiles. The LUT may be determined through empirical studies and by design choice as discussed with respect to other LUTs above. Accordingly, when classifying a capsule by phase change material, the control circuitry detects a temperature at which the capsule remains constant for a period of time and accesses the corresponding heating profile from the LUT using the detected temperature.

For some applications, in cases in which it is desired to prohibit the re-use of already vaporized capsules, the control circuitry is configured to detect a presence of a phase-change material within the capsule. For some applications, the phase-change material is configured to be vaporized, to dissipate, and/or to lose its phase changing properties, in response to the capsule being used, due to its temperature having been increased above its phase-change temperature. The control circuitry is configured to interpret the presence of the phase-change material within the capsule, and/or a characteristic of the phase-change material within the capsule, as indicating that the capsule was not previously vaporized, and to allow the capsule to be heated, only in response thereto. For example, in cases in which re-use of capsules might cause an increased emission of harmful materials or might cause pyrolysis, the control circuitry may be configured as described.

For some applications, a phase-change material is mixed with the plant material within the capsule. Alternatively or additionally, the phase-change material is shaped as a thin plate and is disposed within the capsule such that the phase-change material encapsulates the plant material. In this manner, in addition to the thermal phase-change properties of the phase-change material described hereinabove, the phase-change material facilitates the preservation of and/or reduces the degradation of the plant material, prior to the plant material being heated.

For some applications, respective capsule types are provided with meshes having respective resistance levels. The control circuitry is configured, by measuring the resistance of the mesh, to identify the capsule type that is currently being heated. As described hereinabove, in response to classifying the capsule as a given capsule type, a heating profile that is suited to that capsule type may be applied. For some applications, constructing meshes having respective resistances is performed by using materials with respective resistances, and/or by modifying the mechanical properties of the meshes, such as length, width, cross section, and/or any other property that might influence the resistance. For some applications, a generally similar technique is performed, but the capsules are identified via the electrical resistance of a different portion of the capsules, for example, the main body of the capsules, a resistor embedded in the capsule, and/or resistance of a material within the capsule. In an example embodiment, the control circuitry includes a memory storing a LUT with resistance values in association with corresponding heating profiles. The LUT may be determined through empirical studies and design choice as described above with respect to other LUTs. Accordingly, when classifying a capsule by resistance, the control circuitry measures a resistance of the capsule and accesses the corresponding heating profile from the LUT using the measured resistance.

For some applications, capsules types are identified by use of other types of coding. For example, barcode, unique mechanical features (for example: holes or grooves), switches, electro-optical switches, RFID, or any other applicable coding mechanism.

For some applications, vaporizing unit 21 includes a grill 26, which is configured to allow airflow into the body of the vaporizing unit, as described in further detail hereinbelow. For some applications, a capsule loading and unloading opening 27 is configured to allow the manual and or mechanized loading and unloading of capsules into and out of the vaporization location within the vaporizing unit, as described in further detail hereinbelow.

For some applications vaporizing unit 21 defines a groove 28, which is configured to facilitate insertion of the vaporizing unit into reloading unit 22 in a given alignment. For example, the groove may be configured to facilitate insertion of the vaporizing unit into the reloading unit such that capsule loading and unloading opening 27 is correctly aligned such as to receive a capsule from the first receptacle 53 of the reloading unit, and to deposit capsules into the second receptacle 52 of the reloading unit.

For some applications, the inner surface of mouthpiece 25 (and/or other portions of the vaporizer) includes a lipophobic or hydrophobic coating that is configured to reduce or prevent products of the vaporization of the compound from sticking to the inner surface of the mouthpiece. Alternatively or additionally, a filter (e.g., cellulose acetate filter) is used to filter at least a part of the vapors that pass through the mouthpiece.

The vaporizing unit 21 may be inserted into the reloading unit 22 for the purpose of loading a new capsule into the vaporizing unit 21 (e.g., to the vaporization location of the vaporizing unit), as described hereinabove. Alternatively or additionally, the reloading unit 22 contains a power supply 45 (FIGS. 8A-C and 9A-C). A power supply 33 (e.g., an internal power supply) of the vaporizing unit 21 is configured to become charged by the power supply 45 of the reloading unit 22, by the vaporizing unit 21 being coupled to reloading unit 22. For some applications, the power supply 45 of the reloading unit 22, and/or the power supply 33 of the vaporizing unit 21 is configured to receive power from an external power source, such as mains electricity. The vaporizing unit 21 may be decoupled from the reloading unit 22 prior to using the vaporizing unit 21 to vaporize the compound(s) of the plant material. During the operation of the vaporizing unit 21, the vaporizing unit 21 may be held and may function as an electronic cigarette or vaping device.

Reference is again made to FIG. 6, which is a cross-sectional view of vaporizing unit 21, in accordance with an example embodiment. Reference is also made to FIG. 7, which is a perspective view of internal components of the vaporizing unit 21, in accordance with an example embodiment. The vaporizing unit 21 may include one or more heating elements configured to heat the plant material within capsule 29 (such as to vaporize the compound(s) within the plant material). For some applications, electrodes (e.g., first electrode 36, third electrode 37, fourth electrode 38, and second electrode 39) are configured to act as heating elements, by heating the plant material within the capsule 29, by driving an electrical current into capsule 29. As described hereinabove, for some applications, capsule 29 includes one or more metallic meshes 30 (FIG. 4A-B). The electrodes heat the material inside the capsule by heating the one or more meshes via resistive heating, by driving a current into the one or more meshes. Alternatively or additionally, the electrodes heat an internal heating element that is housed within the capsule, by driving a current into the internal heating element. The electric current that is driven may be controlled, such that, for example, the heating of the capsules is not affected by variations in the degree of contact between the electrodes and the meshes of the capsules.

For some applications, upper mesh of capsule 29 is electrically connected to the lower mesh, and at least two electrodes are used to drive an electrical current into capsule 29. For example, referring to the view shown in FIGS. 6-7, the upper and lower meshes may be electrically connected to one another on one end of capsule 29 via the first electrode 36 and the third electrode 37, and the upper and lower meshes may be electrically connected to one another on the other end of capsule 29 via the fourth electrode 38 and the second electrode 39. For some applications, the lower mesh and/or the upper mesh is heated by the mesh being used to complete a circuit between a pair of electrodes. For example, the plant material contained within the capsule may heated by driving a current from first electrode 36 to second electrode 39 via the lower mesh of capsule 29. Alternatively or additionally, the plant material contained within the capsule may be heated by driving a current from third electrode 37 to fourth electrode 38 via the upper mesh of capsule 29. For some applications, by heating the plant material in the aforementioned manner, the plant material within the capsule is heated more uniformly than if, for example, a monopolar electrode were to drive a current into a location on the upper or lower mesh. For some applications, capsule 29 includes an internal heating element (e.g., an internal mesh (not shown)), as an alternative or in addition to the upper and lower meshes. The internal heating element is configured to be heated in a similar manner to that described with reference to the upper and lower meshes, and is configured to heat the capsule via conductive heating.

For some applications, springs 40 are coupled to at least some the electrodes, e.g., third electrode 37 and fourth electrode 38 as shown in FIG. 7. The springs are configured to push the electrodes towards the capsule 29, in order to improve electrical coupling between the electrodes and the capsule. For some applications, the electrodes include a bladed tip that acts as the electrical contact to the capsule. The tips of the electrodes may have a thickness of more than 0.05 mm (e.g., more than 0.1 mm), and/or less than 0.4 mm (e.g., less than 0.3 mm), e.g., between 0.05 mm and 0.4 mm, or between 0.1 mm and 0.3 mm.

For some applications, an electrode-movement mechanism (not shown) is configured to move at least a portion of the electrodes with respect to a mesh of capsule 29. For example, an electrode-movement mechanism as described in WO 16/147188 to Raichman, the entire disclosure of which is incorporated herein by reference, may be used. For example, the electrode-movement mechanism may move the electrodes closer to the mesh, and/or may move the electrodes with respect to the mesh (e.g., by sliding the electrodes across the surface of the mesh), while the electrodes are in contact with the mesh. In this manner, the electrodes may remove at least a portion of a coating that has developed on the surface of the mesh, and/or penetrate the coating. For some applications, the electrode-movement mechanism is configured to move the electrodes away from the mesh, for example, in order to facilitate insertion of a capsule into the vaporization location or removal of a capsule from the vaporization location, in a manner that friction between the capsule and the electrodes is reduced or eliminated.

Although vaporizing unit 21 has been described as using resistive heating of the first electrode 36, the third electrode 37, the fourth electrode 38, and/or the second electrode 39 to heat capsule 29, for some applications, alternative or additional heating elements and heating techniques are used to heat the capsule. For example, a laser emitter may act as a heating element by directing a laser beam at the capsule, in order to heat the capsule. For some applications, a separate heating element that is housed inside the vaporizing unit is heated in proximity to the vaporization location, in order to provide conduction, convection, and/or radiation heating to the capsule.

During use of the vaporizing unit, a subject draws or inhales from the mouthpiece 25. This causes air to flow through grill 26 (FIG. 5) to the mouthpiece via the capsule, as indicated by the dashed airflow arrow in FIG. 6. The capsule may be configured to be placed at the vaporization location within the vaporizing unit, such that planes defined by the upper and lower meshes are perpendicular to a direction of the air flow through the vaporizer at the vaporization location. For some applications, a sealing gasket 41 is used to reduce or prevent air from outside the vaporizing unit from flowing into mouthpiece 25 without passing through capsule 29. In a non-limiting embodiment, the control circuitry 34 includes any well-known puff sensor to detect draw or inhalation.

A power supply 33 (e.g., a battery) and control circuitry 34 may be housed inside the body of vaporizing unit 21. The power supply 33 and/or the control circuitry 34 may be coupled to the body of the vaporizing unit 21 by a coupling element, such as an adhesive, a screw, a clip, and/or a pin. For some applications, the control circuitry 34 is configured to drive a current into the capsule 29 via the first electrode 36, the third electrode 37, the fourth electrode 38, and/or the second electrode 39, using power supplied by the power supply 33.

The control circuitry 34 may be as previously described above and/or comprise electronic components, such as resistors, transistors, capacitors, inductors, and diodes. For some applications, the control circuitry 34 includes a computer processor and associated memory. The computer processor may act as a special purpose vaporization-controlling computer processor by executing code stored on the memory. The operations described herein that are performed by such a computer processor may also result in data being accessed and/or stored in memory; and thus, transform the physical state of a memory, which is a real physical article, to have a different magnetic polarity, electrical charge, or the like depending on the technology of the memory that is used.

For some applications, the vaporizing unit 21 includes a temperature sensor 35 that is configured to measure an indication of the temperature of the material that is being heated, e.g., by measuring the temperature of the capsule that is being heated. For example, the temperature sensor 35 may be an optical temperature sensor, such as an infrared temperature sensor, that is configured to measure the temperature of the capsule without contacting the capsule. FIGS. 6-7 show the temperature sensor 35 aligned to receive beams of optical light from capsule 29 (the capsule 29 having been heated). The temperature sensor 35 is configured to measure the temperature of capsule 29, based upon the received light. In this manner, the optical temperature sensor measures the temperature of the capsule 29, without affecting the temperature of the capsule 29 by drawing heat from the capsule 29. For some applications, the temperature sensor 35 is covered with a lipophobic or hydrophobic coating that protects the temperature sensor 35 from products of the vaporization being deposited upon the temperature sensor 35. The temperature sensor 35 may have a "near zero" response time, such that the control circuitry is able to measure changes in temperature due to changes in airflow, and respond to such changes in the manner described hereinbelow, effectively immediately with respect to the perception of the subject. For example, the temperature sensor may be configured to detect in real time changes in temperature, e.g., within 0.01 seconds (e.g., within 1 millisecond) of such changes. For some applications, by virtue of having such a temperature sensor, the control circuitry is configured to respond in real time to airflow-induced changes in temperature, e.g., within 0.01 seconds (e.g., within 1 millisecond) of such changes.

For some applications, vaporizing unit 21 includes a fan 48 (FIG. 6) that is configured to vent out vapors during the heating process, by ventilating a space between temperature sensor 35 and the capsule 29. During the heating of the plant material, vapors may be emitted. In some cases, in the absence of the fan 48, the vapors may mask the capsule 29 and/or the plant material from temperature sensor 35. In turn, this may cause errors in the temperature that is measured by the temperature sensor 35 (and particularly if temperature sensor 35 is an infrared temperature sensor). For example, the temperature sensor 35 may measure the temperature of the plant material as being lower than it actually is, which could lead to the plant material being overheated, causing damage, pyrolysis, and/or or ignition of the plant material. Therefore, for some applications, a fan 48 vents vapors from the vaporizing unit 21 during at least a portion of the heating process, by driving air into and/or out of the vaporizing unit. Alternatively or additionally, unwanted vapor accumulation within the device may be reduced by designing internal passages of the device with dimensions that are such to allow air flow between the temperature sensor 35 and the plant material that is sufficient to reduce or prevent vapor accumulation.

For some applications, a different temperature sensor is used. For example, the control circuitry 34 may detect the temperature of the capsule 29 by detecting changes in the resistance of components of the capsule 29 (e.g., mesh 30 of the capsule 29) using the first electrode 36, the third electrode 37, the fourth electrode 38, and/or the second electrode 39. In an example embodiment, the control circuitry includes a memory storing a LUT. The LUT stores resistance values in association with corresponding temperature values. The LUT may be determined through empirical studies. Accordingly, during operation, the control circuitry measures a resistance of the capsule and accesses the corresponding temperature value from the LUT using the measured resistance. In instances where a measured resistance is between two adjacent resistance values in the LUT, the control circuitry is configured to use the first adjacent resistance value in the LUT as a first index and the second adjacent resistance value in the LUT as a second index. Based on the relative position of the measured resistance between the first and second indexes, the control circuitry interpolates the corresponding temperature from the temperatures accessed using the first and second indexes (e.g., by performing a weighted average or straight average).

For some applications, the vaporizing device 20 includes a port (not shown) via which the vaporizing device 20 is connected to an external source of power and/or data input. For example, power supply 45 of reloading unit 22 may be configured to be recharged by connecting the vaporizing device to an external power supply (e.g., mains electricity) via the above-mentioned port. Alternatively or additionally, control circuitry 34 may receive data, e.g., programming instructions, via above mentioned port.

For some applications, instructions may be input into the control circuitry that control the amount of heat that is applied for a given rate of airflow through the capsule. For example, the instructions may be input via a user interface 10 (such as a touchscreen display, or buttons), shown in FIG. 3, that is coupled to the control circuitry. Alternatively or additionally, the instructions may be input via a computer, a tablet device, a phone, and/or a different telecommunications device that communicates with the control circuitry via a wired or a wireless communications protocol. For example, a heating profile that is desired may be indicated, and the control circuitry may control the amount of heat that is applied for a given rate of airflow through the capsule, in response thereto. For some applications, the control circuitry is configured to automatically determine the heating profile, based upon the rate of airflow through the vaporizing unit (e.g., through the capsule), as described in further detail hereinbelow. By controlling the amount of heat that is applied for a given rate of airflow through the capsule, the amount of the compound that is vaporized per unit airflow rate through the vaporizer may be controlled. For some applications, vaporizing unit 21 includes an airflow sensor, (not shown). For some applications, the control circuitry is configured to automatically determine the rate of airflow through the vaporizer, by detecting the temperature of the capsule, as described in further detail hereinbelow.

For some applications (not shown), the vaporizing unit 21 is shaped to define a supplementary airflow channel, which provides airflow out of mouthpiece 25, but not via the capsule that is being vaporized (not shown). In this manner, in response to a relatively large inhalation, the vaporizer is able to provide air, without increasing the dosage of the compound.

For some applications, the control circuitry 34 of the vaporizing unit or control circuitry of the reloading unit (not shown) includes one or more indicators for generating alerts. For example, the control circuitry may illuminate an indicator light, may cause the vaporizing unit to vibrate, and/or may emit an audio signal (e.g., a beep). Alternatively, the vaporizing unit may include user interface 10, which may include a display (e.g., an LED or LCD display), and the control circuitry may generate an alert on the display. For some applications, the control circuitry is configured to generate an alert in response to sensing that, during inhalation or draw from the vaporizer, the temperature of the plant material is less than a given threshold temperature. Alternatively or additionally, the control circuitry is configured to generate an indication in response to sensing that the temperature of the plant material is greater than a given threshold temperature (e.g., a temperature of more than between 300 degrees Celsius and 350 degrees Celsius), which may cause the material to become pyrolyzed or ignite. For some applications, the threshold is established with respect to an expected target temperature. For example, an alert may be generated in response to sensing a temperature that is 50 degrees Celsius less than an expected target temperature. Furthermore, alternatively or additionally, the control circuitry is configured to generate an indication that a capsule is faulty, is incorrectly placed, and/or is missing, in response to measuring a temperature that is less than a given threshold, during the heating process.

Figure 9C:
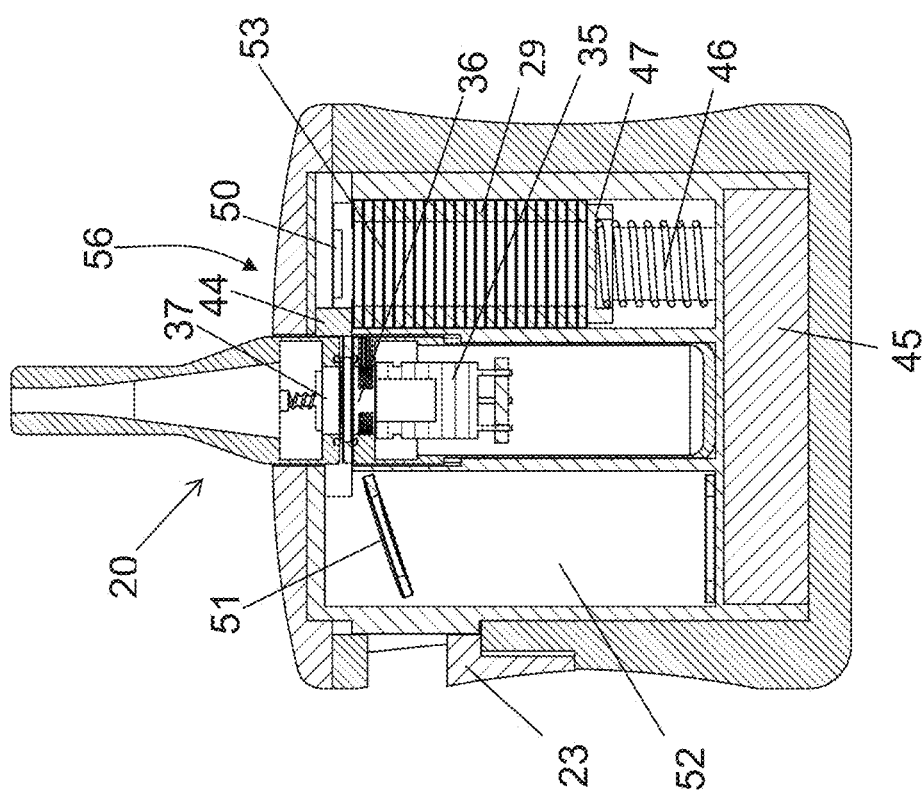

Reference is now made to FIGS. 8A-C, which are perspective views of inner components of the reloading unit 22 with a vaporizing unit 21 disposed therein, at respective stages of an operation of capsule-loading mechanism 56, in accordance with an example embodiment. Reference is also made to FIGS. 9A-C, which are cross-sectional views of the vaporizing device 20, showing the vaporizing unit 21 placed in a portion of reloading unit 22, at respective stages of an operation of capsule-loading mechanism 56, in accordance with an example embodiment.

The reloading unit 22 of the vaporizing device 20 may include the first receptacle 53 and the second receptacle 52 (shown in FIG. 9C), which are configured to house capsules 29. Unused capsules may be housed in a stacked configuration (i.e., such that when the vaporizing device is in an upright orientation, the capsules are arranged one above the other) inside first receptacle 53, and used capsules are housed in a stacked configuration inside second receptacle 52. A spring 46 and a pushing element 47 may be coupled to a bottom of first receptacle 53. The spring and pushing element are configured to maintain the stacked configuration of the capsules inside the first receptacle by pushing the capsules toward the top of the first receptacle within the reloading unit. For some applications, by storing the capsules in stacked configurations, the dimensions of the width and depth of the vaporizing device 20 may be such that the vaporizing device can be comfortably held (e.g., within a single hand) or carried in a pocket.

For some applications, capsules 29 have circular cross-sections, and the first receptacle 53 and the second receptacle 52 define cylindrical tubes that house the capsules. Alternatively, capsules 29 may have a different shape, and the first receptacle 53 and the second receptacle 52 may define hollow spaces that are shaped so as to conform with the shapes of the capsules. For example, as shown in FIG. 4A, the capsules may have a racetrack-shaped cross section.

The capsule-loading mechanism 56 may be configured to (a) individually transfer unused capsules from first receptacle 53 inside reloading unit 22 to vaporization location 54 (FIG. 6) inside vaporizing unit 21, at which location the capsule is heated such as to vaporize the compound(s) of the plant material, and (b) to individually transfer used capsules from the vaporization location to second receptacle 52 located inside reloading unit 22.

For some applications, the vaporizing unit 21 is configured to become coupled to reloading unit 22, such that the top of the first receptacle 53 and the top of the second receptacle 52 inside reloading unit 22, and vaporization location 54 (FIG. 6) inside vaporizing unit 21, are linearly aligned with each other (for example, across the width of the vaporizing device, as shown in FIGS. 9A-C). For some such applications, capsule-loading mechanism 56 is a linear capsule-loading mechanism, configured to move each of the capsules by moving linearly. The capsule-loading mechanism is configured to push unused capsules from the first receptacle 53 to vaporization location 54 (FIG. 6) at which location the capsule is heated, and from the vaporization location to second receptacle 52 inside reloading unit 22.

As described hereinabove, for some applications, the first receptacle 53 of reloading unit 22 houses pushing element 47 and spring 46, which is coupled to the pushing element. For some applications, an upper capsule stopper 50 is used in the upper part of the first receptacle 53. The upper capsule stopper 50 is configured to limit the upmost position of the upper capsule of the stack within the first receptacle 53, such that the possibility of the upper capsule blocking or disturbing the movement of capsule-loading mechanism 56 is reduced or prevented.

For some applications, a capsule-loading button 23 is used in order to linearly move capsule-loading mechanism 56. Alternatively or additionally, capsule-loading mechanism 56 is configured to be moved by an electrical motor (not shown) that is controlled by control circuitry inside reloading unit 22.

Reference is now made to FIGS. 8A and 9A, which illustrate the capsule-loading mechanism 56 in its initial rest stage. At this stage, springs 42 apply force to a capsule-engagement plate 44 of capsule-loading mechanism 56, causing the capsule-engagement plate 44 to be located at the beginning of its linear travel path (at the right-most position, as shown in FIGS. 8A and 9A). At this position, the capsule-engagement plate is configured to engage the uppermost capsule of the stack of capsules in the first receptacle 53, ready for the beginning of a new capsule loading cycle.

Reference is now made to FIGS. 8B and 9B, which illustrate the capsule-loading mechanism 56 in a second stage of its operation, during the loading of an unused capsule from the top of the first receptacle 53 inside reloading unit 22, into the vaporization location 54 (FIG. 6) inside vaporizing unit 21. For some applications, in order to reload a new unused capsule into the vaporizing unit 21, the capsule-loading button 23 is pressed downwards. For some such applications, the capsule-loading button 23 is coupled to a pinion circular gear 43 and configured such that, when the capsule-loading button 23 is pressed, its linear downwards motion turns the pinion circular gear 43. For some such applications, a rack linear gear 49 is disposed on capsule-engagement plate 44, and is configured to engage pinion circular gear 43, such that circular movement of pinion circular gear 43 is transformed into a linear motion of capsule-engagement plate 44 from its initial position towards the vaporization location 54 (FIG. 6) inside vaporizing unit 21. The above-mentioned movement of capsule-engagement plate 44 pushes the upper-most unused capsule within the first receptacle 53 into the vaporization location 54 (FIG. 6) inside vaporizing unit 21. In some cases, a used capsule 51 from a previous vaporization is positioned in the vaporization location prior to the reloading of a new unused capsule. The capsule-loading mechanism 56 may be configured such that insertion of the unused capsule into the vaporization location 54 by the capsule-loading mechanism 56, pushes the used capsule 51 out of the vaporization location 54 toward the second receptacle 52.

For some applications, as shown, pinion circular gear 43 includes a combination of two circular gears with different radii, such as to create a transformation ratio that reduces the downwards distance through which the capsule-loading button 23 must be moved, in order to move capsule-engagement plate 44 from its initial position to its end position, relative to if a single circular gear were to be used.

Reference is now made to FIGS. 8C and 9C, which illustrate the capsule-loading mechanism 56 in a final stage of its operation. At this stage, as shown, the capsule-loading button 23 may be fully pressed such that the capsule-engagement plate 44 fully places a new, unused capsule into vaporization location 54 (FIG. 6) so as to be ready for heating. Previously used capsule 51 is fully emitted out of vaporizing unit 21 into the second receptacle 52 and springs 42 are fully compressed. For some applications, as the capsule-loading button 23 is released, springs 42 push capsule-engagement plate 44 back to its initial rest point (as shown in FIGS. 8A and 9A). The capsule-loading button 23, which is coupled to capsule-engagement plate 44 by the abovementioned rack and pinion gears, may be automatically pushed back its initial position by the rack and pinion gears so as to be ready for a new capsule loading cycle.

For some applications, reloading unit 22 includes an indicator 58 (FIG. 1) that indicates how many unused capsules are housed within the reloading unit 22. For some applications, rather than the reloading unit being configured to be refilled, some of the components of vaporizing device 20 are recyclable and are transferrable to an unused reloading unit. For example, a single vaporizing unit 21 could be used with a plurality of reloading units, each of which is configured for single use. For some applications (e.g., applications in which the device is used with *cannabis* that is administered for medicinal purposes), the size of the capsules and/or the amount of plant material in each capsule that is to be provided may be determined by a healthcare professional. In addition, as described hereinabove, the vaporizing device may be programmable, such that, for example, only a certain dosage of the compound may be released per use, per puff, or within a given time period. In this manner, if the plant material that is used inside the vaporizing device is a regulated substance (e.g., *cannabis*), control over the use of the substance may be maintained. For some applications, the vaporizing device, the reloading unit, the vaporizing unit, and/or the capsules include identifying marks or tags (e.g., an RFID or a barcode), such as to facilitate regulation and control of the use of the vaporizing device and the capsule.

For some applications, reloading unit 22 does not include the second receptacle 52, and previously used capsules are ejected from the vaporization location out of the vaporizing unit without being stored inside the reloading unit. For some applications, the capsule-loading button 23 and the pinion circular gear 43 are not used and an electrical motor is coupled to capsule-engagement plate 44, such as to generate the linear movement for capsule loading. For some applications, a different type of capsule-loading mechanism is used, mutatis mutandis. For example, a capsule-loading mechanism may be used that is generally similar to any one of the capsule-transfer mechanisms as described in WO 16/147188 to Raichman, the entire disclosure of which is incorporated herein by reference.

Figure 10:
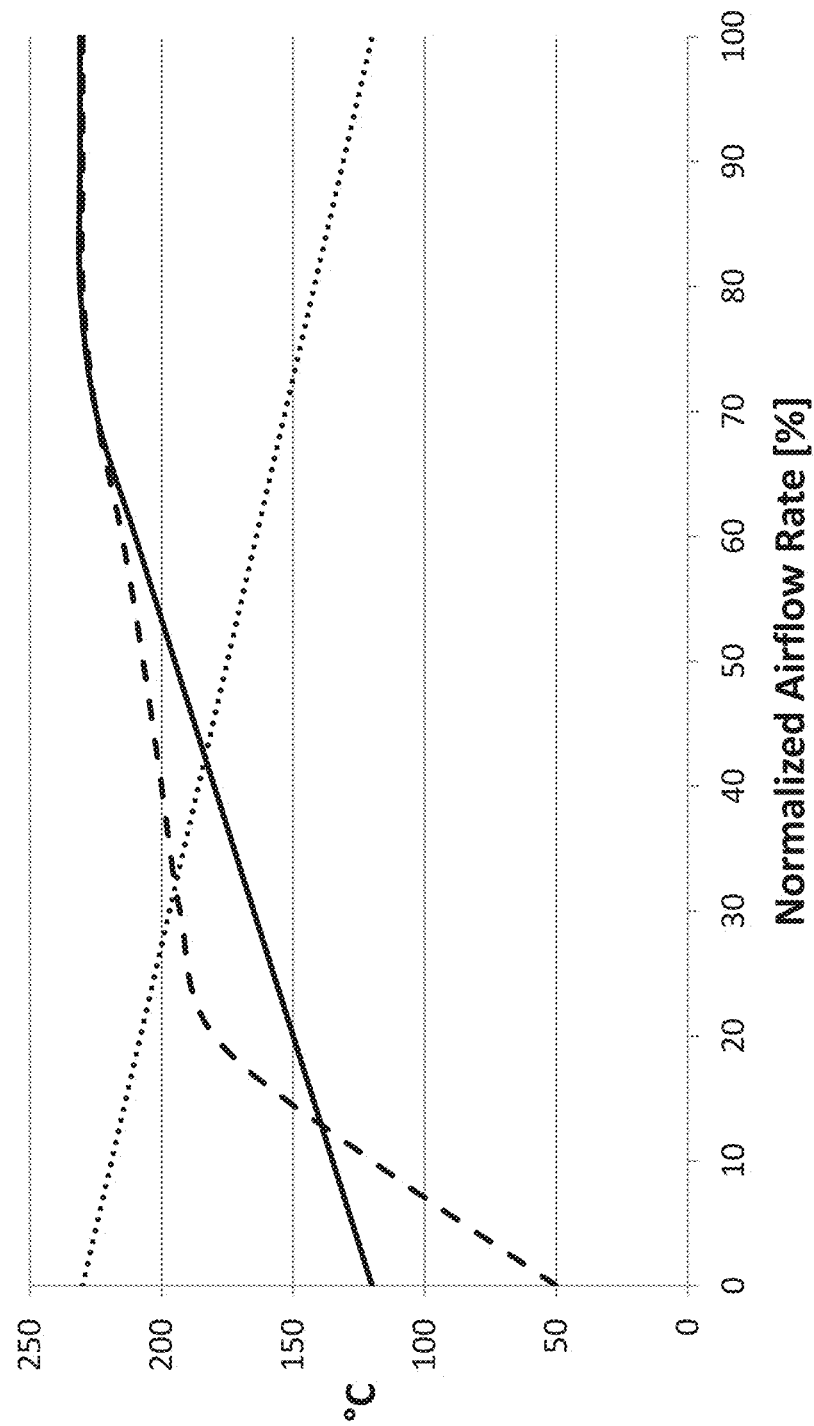
FIG. 10 is a graph illustrating a technique for heating a capsule containing a material, in accordance with an example embodiment.

Reference is now made to FIG. 10, which is a graph with respective curves illustrating respective techniques for heating a material (e.g., plant material) using a vaporizer, such as vaporizing unit 21, in accordance with an example embodiment. The x-axis of the graph indicates normalized airflow rate (measured as a percentage), and the y-axis indicates the temperature (measured in degrees Celsius) to which the control circuitry controls the heating of a capsule at a given airflow rate. The airflow rate percentage may be measured with reference to an upper or maximal airflow rate (e.g., when a subject draws or inhales from the vaporizer). By way of example, the airflow rate may be measured as a percentage of an airflow rate of between 0.8 and 1.2 liters per minute. In an example embodiment, the control circuitry includes a memory storing a LUT with airflow values indexing to corresponding temperature values at which the capsule is to be heated. The LUT may be determined through empirical studies. For example, the LUT may implement one of the curves shown in FIG. 10. Accordingly, during operation, the control circuitry receives an indication of an airflow through the capsule (e.g., from the airflow sensor) and accesses the corresponding temperature value from LUT using the airflow. The control circuitry then controls the heater to heat the capsule to the accessed temperature. In instances where a measured airflow is between two adjacent airflow values in the LUT, the control circuitry is configured interpolate the temperature at which the capsule is to be heated (e.g., by performing a weighted average or straight average) from the two accessed temperatures such as described previously.

As described hereinabove, for some applications, a vaporizing unit 21 is used to vaporize the compounds within *cannabis*. In other instances, the vaporizing unit 21 is used to vaporize the compounds within tobacco. Tobacco may have a vaporization temperature of 150 to 230 degrees Celsius and may begin to become pyrolyzed at 250 degrees Celsius. Therefore, it may be desirable to heat the tobacco to a temperature of between 150 degrees Celsius and 230 degrees Celsius. Furthermore, it may be desirable not to heat the tobacco to a temperature that is greater than 230 degrees Celsius, in order to reduce or prevent pyrolysis of the tobacco. When the vaporizer is used with materials other than tobacco, similar considerations may be applicable, although the desired temperature to which the material should be heated will vary depending on the characteristics of the material that is being used with the vaporizing unit.

Mouthfullness is an attribute that relates to the texture and feel of a vapor in the mouth. By controlling the draw or inhalation rate, a subject can adjust the mouthfullness according to their personal taste and preferences.

For some applications, the feeling of mouthfullness is at least partially replicated when using a vaporizer (for example, vaporizing unit 21) by heating the plant material within the capsule as a function of airflow rate through the vaporizer (for example, air flow through capsule 29 shown in FIG. 6), which is indicative of the draw or inhalation rate. This may enable control over at least some of the properties of the generated vapors.

For some materials (for example, tobacco and *cannabis*), increasing the temperature of the capsule causes an increase in the vaporization rate of the compound, with more vapors being emitted as temperature is set higher. For some materials, increase of vaporization temperature influences the taste of the generated vapors. Some materials (for example, various types of tobacco), when heated to the lower end of their vaporization temperature range, emit light tasted vapors, and when heated to higher temperatures within their vaporization temperature range, generate vapors having a different taste, e.g., more heavy, rich, woody, or smoked.

For some applications, the plant material is initially heated to a temperature point at the lower end of the vaporization temperature range of the plant material. The temperature is then increased within the vaporization temperature range according to a function of the detected inhalation air flow through the vaporizer (e.g., through the capsule of the vaporizer), with the maximum temperature to which the capsule is heated being limited in some applications, in order not to exceed the plant material's pyrolysis temperature. For some applications, the plant material is heated to a lower temperature when lower airflow rate is detected and to a higher temperature when a high airflow rate is detected. For example, the temperature to which the capsule is heated may be increased in direct proportion to increases in the normalized airflow through the vaporizer, as denoted by the solid curve in FIG. 10. Also, as shown by the solid curve of FIG. 10, for some applications, when the capsule is heated to a maximal temperature (of approximately 230 degrees Celsius, as shown in FIG. 10), additional heating is withheld, e.g., to avoid reaching the pyrolysis temperature of the plant material.

For some applications, the capsule containing the plant material is initially heated to a temperature point below the lower end of the vaporization temperature range of the plant material. When little to no air flows through the capsule, the sub-vaporization temperature of the plant material will reduce or prevent the vaporization of the compound. Upon detection of an increase in airflow rate, the control circuitry rapidly increases the temperature of the plant material to a point within the vaporization temperature range of the plant material. On detection of an additional increase in inhalation air flow, the capsule temperature is adjusted according to the detected airflow rate.

For some applications, in response to receiving a first input at the vaporizer (e.g., in response to the pressing of an ON switch on the vaporizer), the control circuitry of the vaporizer initiates a pre-heating step. The pre-heating step may be a rapid heating step (e.g., a heating step in which the capsule that contains the plant material is heated at a rate of more than 50 degrees Celsius per second, or more than 100 degrees Celsius per second). Furthermore, the control circuitry of the vaporizer may be configured to terminate the first heating step, thereby discontinuing a further temperature increase of the capsule, in response to detecting that the temperature of the capsule (which is indicative of the temperature of the plant material) has reached a first temperature. The first temperature may be more than 80 percent and less than 120 percent of the low end of the plant material vaporization range, e.g., more than 90 percent and less than 110 percent, or more than 85 percent and less than 95 percent, or more than 105 percent and less than 115 percent of the low end of the used vaporization temperature range. For example, when the vaporizer is used to vaporize tobacco, the control circuitry of the vaporizer may be configured to stop increasing the temperature of the capsule, in response to detecting that the temperature of the capsule has reached a temperature that is less than 170 degrees Celsius (e.g., less than 150 degrees Celsius), e.g., a temperature that is between 120 and 130 degrees Celsius, or between 130 and 140 degrees Celsius. For some applications, in response to the detection of airflow through the plant material, the plant material's temperature is increased at a rate of between 0.5 to 10 degrees Celsius per percent of airflow rate increase, e.g., a temperature increase of 0.5 to 2 degrees Celsius, 2 to 8 degrees Celsius, or 5 to 10 degrees Celsius per percent of airflow rate increase.

In a non-limiting embodiment, the control circuitry may be configured to place the vaporizer in standby mode if a second input (e.g., a draw or inhalation) is not detected within a period of time. The period of time may be design parameter determined through empirical study.

For some applications, to enable the performing of airflow rate related heating of the plant material, the vaporizer (for example vaporizing unit 21) is configured to enable fast heating of the plant material in order to rapidly adjust the temperature of the plant material to changes in the airflow rate during the inhalation, for example, to enable a temperature increase of more than 20 degrees Celsius per second (e.g., more than 50 or more than 100 degrees Celsius per second). For some applications, the target temperature to which the plant material is heated is dynamically updated in order to adjust the vaporization temperature and vaporization rate according to the heating profile. For some applications, the target temperature to which the plant material is heated is dynamically updated in a continuous manner. For some applications, the capsule is heated to a target a temperature that is derived as a continuous function of the detected airflow rate. For example, the continuous function may be a polynomial function, a monotonically increasing function, a monotonically decreasing function. Alternatively, the target temperature to which the plant material is heated is dynamically updated on a puff-by-puff basis, i.e., with each inhalation, the control circuitry calculates a target temperature to which the capsule should be heated for that inhalation. For some applications, the control circuitry detects a draw or inhalation based on an input via an interface located on the reloading unit or the vaporizing unit. Alternatively or additionally, the control circuitry detects a draw or inhalation by detecting the temperature of the capsule, and/or by detecting an indication of an amount of energy required to maintain the temperature of the capsule constant. For example, if the amount of energy required to maintain the temperature of the capsule constant exceeds a threshold value, then the control circuitry detects a draw or inhalation. The threshold value may be a design parameter determined through empirical study.

For some applications, the control circuitry of the vaporizer calculates the airflow rate through the capsule by measuring the electrical power needed to maintain the capsule that houses the plant material at a desired temperature. In an example embodiment, the control circuitry includes a memory storing a LUT with power values stored in association with corresponding airflow values. The LUT may be determined through empirical studies. Accordingly, during operation, the control circuitry measures a power level needed to maintain the capsule temperature and accesses the corresponding airflow value from the LUT. In instances where a measured power level is between two adjacent power levels in the LUT, the control circuitry is configured to use the first adjacent power level as a first index and the second adjacent power level as a second index. Based on the relative position of the measured power level between the first and second indexes, the control circuitry interpolates the airflow through the capsule (e.g., by performing a weighted average or straight average) using the airflows accessed from the LUT using the first and second indexes.

In order to enable the use of this technique for airflow measurement, the plant material may be initially heated to a temperature that is above the ambient air temperature, for example to 50 degrees Celsius or more (as shown by the dashed curve in FIG. 10), or to 120 degrees Celsius or more (as shown by the solid curve in FIG. 10). Once the capsule has been heated above the ambient temperature and ambient air is then made to flow through the capsule as a result of a draw or inhalation, the electrical power needed to maintain the capsule at a given temperature may be related to airflow rate and the temperature gradient between the capsule and the flowing ambient air. Therefore, the control circuitry is configured to determine the airflow rate based upon the current temperature of the capsule, and the electrical power needed to maintain the capsule at the temperature. For example, the control circuitry may determine the electrical power needed to maintain the capsule at the temperature by detecting variations in the duty cycle that is used to heat the capsule.

In an example embodiment, the control circuitry includes a memory storing a LUT with duty cycle variation values stored in association with corresponding power values needed to maintain the capsule temperature. The LUT may be determined through empirical studies. Accordingly, when the duty cycle is detected to exceed a lower threshold, the control circuitry determines that the device is in operation and measures the duty cycle variation and accesses the corresponding power value from the LUT. In instances where a measured duty cycle variation is between two adjacent duty cycle variation values in the LUT, the control circuitry is configured to use the first adjacent duty cycle variation value as a first index and the second adjacent duty cycle variation value as a second index. Based on the relative position of the measured duty cycle variation between the first and second indexes, the control circuitry interpolates the power level needed to maintain the capsule temperature (e.g., by performing a weighted average or straight average) using the power levels accessed from the LUT using the first and second indexes.

In another example embodiment, the control circuitry includes a memory storing a LUT with temperature and power values stored in association with corresponding airflow values through the capsule. The LUT may be determined through empirical studies. Accordingly, when the duty cycle is detected to exceed a lower threshold, the control circuitry determines that the device is in operation and measures the temperature and power values and uses these as inputs to access the corresponding airflow value from the LUT.

For some applications, the temperature of the capsule is not held constant, and the control circuitry determines the airflow rate through the capsule at least partially based upon measured changes in temperature of the capsule resulting from changes in airflow rate through the capsule. For example, the control circuitry may continue to heat the capsule at a fixed power, and measure the changes in temperature of the capsule. Such changes in temperature are indicative of the airflow rate through the capsule. In an example embodiment, the control circuitry includes a memory storing a LUT with temperature differences for a given period of time stored in association with corresponding airflow values. The LUT may be determined through empirical studies. Accordingly, during operation, the control circuitry measures a temperature difference of the capsule over the given period of time and accesses the corresponding airflow value from the LUT. In instances where a measured temperature difference is between two adjacent temperature differences in the LUT, the control circuitry is configured to use the first adjacent temperature difference as a first index and the second adjacent temperature difference as a second index. Based on the relative position of the measured temperature difference between the first and second indexes, the control circuitry interpolates the airflow through the capsule (e.g., by performing a weighted average or straight average) using the airflows accessed from the LUT using the first and second indexes.

Alternatively, the control circuitry may stop heating the capsule when the capsule is at a given temperature, and measure changes in the temperature of the capsule. Such changes in temperature may be correlated with the rate of airflow through the capsule, since the measured change in temperature is indicative of induced heat transfer from the heated capsule to the ambient air, by convection, which, in turn, is indicative of the rate of airflow through the capsule. For some applications, the control circuitry is configured to measure ambient temperature and/or humidity in order to calculate airflow rate in accordance with the technique described herein. In order to calculate the airflow rate, the control circuitry may account for the difference between the temperature of the capsule (and therefore the plant material), and the ambient temperature. In an example embodiment, the control circuitry includes a memory LUT with temperature differences for a given period of time, temperature differences relative to ambient, and humidity values stored in association with corresponding airflow values. The LUT may be determined through empirical studies. Accordingly, during operation, the control circuitry measures at least one of a temperature difference of the capsule over the given period of time as a first input, a temperature difference of the capsule relative to an ambient temperature as a second input, and a humidity of the capsule as a third input. With one or more of these inputs, the control circuitry accesses the corresponding airflow value from the LUT.

For some applications, functions or lookup tables (LUT) are used to determine the target temperature to which the capsule is heated, based upon the detected airflow rate indication, according to the material in use, the desired experience or any other relevant factor. For some applications, in addition to airflow rate measurement, inputs are received by the control circuitry from additional sources, in order to determine the target temperature to which to heat the capsule. For example, as described hereinabove, the control circuitry may be configured to classify a capsule as a given capsule type, and to control the heating of the capsule based upon a heating profile that is specifically suited to that capsule type. For example, different types of capsules may have different airflow-rate-to-target-capsule-temperature profiles applied to them. For example, one type of capsule may follow a profile as indicated by the solid curve of FIG. 10, another capsule type may follow a profile as indicated by the dashed curve of FIG. 10, and yet another capsule type may follow a profile as indicated by the dotted curve of FIG. 10. For some applications, a desired heating profile may be input using a subject interface 10 (shown in FIG. 3).

For some applications, by performing the heating of the capsule in the airflow related process described hereinabove, one or more of the following results are achieved:

1) For some applications, the target temperature to which the capsule is heated is correlated to airflow rate (which is indicative of draw or inhalation rate). As described in the examples hereinabove, the capsule is not heated above a maximal temperature limit (which may be less than 90 percent of the pyrolysis temperature of the plant material). The maximal temperature limit may be set such that the plant material is not heated to a temperature that is greater than the pyrolysis temperature of the plant material, and/or such that the plant material is not heated to a temperature that will produce smoke and/or an unpleasant taste. By dynamically adjusting the target vaporization temperature as described hereinabove, the taste and "mouthfullness" of the generated vapors are adjusted according to individual taste and preferences. For example, subjects who prefer a longer and slower inhalation may benefit from receiving a relatively constant and slow supply of the vaporized compound, due to the relatively lower vaporization temperature that will be generated by the lower airflow rate of the slower inhalation. On the other end, subjects who prefer a faster and more intense release of the compound may enjoy the higher vaporization rate that will result from the higher vaporization temperature to which the plant material is heated, due to their elevated inhalation airflow rate.

2) Dynamically adjusting the target temperature to which the plant material is heated as described hereinabove, may provide higher efficiency in the consumption rate of the plant material. For example, subjects who prefer taking several relatively short puffs will not suffer from loss of plant material between the shorter puffs, since the control circuitry will lower the target temperature to which the capsule is heated between the puffs.

3) Dynamically adjusting the target temperature to which the capsule is heated as described hereinabove, may reduce loss of compound(s) prior to the beginning of inhalation. The lack of airflow prior to the inhalation will result in the target temperature to which the capsule is heated being relatively low, such as to reduce vaporization of the compound(s) prior to inhalation.

4) In some cases, a delivery of a constant dose of the compound is desired on every puff. For a given arrangement of plant material, the mass of the compound that is vaporized is a function of, at least, the temperature of the material and of the airflow rate through the material. For some applications, an airflow-related heating process is used as described hereinabove, and the control circuitry responds to the measured airflow indication, such as to deliver a constant dose of the compound for each puff of the vaporizing unit. For example, a function or LUT may be used in accordance with which the vaporization temperature is reduced in response to the airflow increasing.

5) For some applications, the control circuitry additionally accounts for the amount of compound that has already been vaporized from the portion of the plant material that is currently being heated (which may, for example, be a portion of the plant material that is disposed inside a capsule). For example, in some cases, based on the rates of airflow and temperatures that have already been applied to the capsule that is currently being heated, the control circuitry may determine an amount of the compound that has already been vaporized. For some applications, the control circuitry determines the target temperature to which to heat the capsule, in response to the amount of compound that has already been vaporized. For some applications, the control circuitry determines the target temperature to which to heat the capsule, in response to (a) the amount of compound that has already been vaporized, as well as (b) the measured airflow through the vaporizing unit (e.g., through the plant material that is being heated within the vaporizing unit). For example, for a given airflow rate, the control circuitry may heat the capsule to a greater temperature as more of the compound becomes vaporized. This may be because, once a given amount of the compound has already been vaporized from the plant material, the plant material may need to be heated to a greater temperature in order for the remaining compound to be vaporized. For some applications, in response to determining that a given amount of the compound has already been released from the plant material, the control circuitry may be configured to reduce the temperature of the plant material to a sub-vaporization temperature, such as to withhold additional vaporization of compound. These controls may be implemented using empirically derived functions or LUTs as described previously above.

For some applications, in response to the detected or determined rate of air flow through the vaporizer, the control circuitry calculates the dosage of the compound that has been provided. For some applications (e.g., when the vaporizer is used with *cannabis* for medicinal purposes), a healthcare professional inputs instructions and/or LUTs into the control circuitry that control the amount of airflow through the vaporizer that is permitted during each use of the vaporizer, and/or the amount of airflow through the vaporizer that is permitted within a given time period (e.g., per hour, or per day, or per puff). Alternatively or additionally, the control circuitry may control the heating rate per unit airflow rate, as described hereinabove. For example, in order to deliver a constant dose of one or more compounds, the control circuitry may be configured to decrease the temperature to which the capsule is heated, in response to detecting an increase in the airflow, as indicated by the dotted curve in FIG. 10. For some applications, the decrease in temperature is configured to keep a constant vaporization rate. For some applications, the control circuitry combines the aforementioned temperature control functionality with setting a time limit for the heating that is applied in response to each puff of the vaporizer. In this manner, a constant dose of one or more compounds is delivered with each puff, regardless of the airflow rate of the puff.

For some applications, in response to detecting that no draw or inhalation has occurred over a given time period (e.g., a time period of between 0.5 seconds and 3 seconds), the control circuit reduces the temperature of the capsule to below the vaporization temperature of the plant material. For example, during use of the vaporizer, a subject may stop inhaling for a given time period. By reducing the temperature to below the vaporization temperature, wastage of the plant ingredient during this period is reduced.

Referring again to FIG. 10, for some applications a heating profile is applied as indicated by the solid curve. For example, between approximately 0 airflow rate percentage units and 70 airflow rate percentage units the control circuitry causes the temperature of the capsule to be modified along a temperature range of 120 to 230 degrees Celsius. This is performed by detecting the current inhalation airflow rate and adjusting the temperature according to the curve. From approximately 70 airflow rate percentage units to 100 airflow rate percentage units, the capsule maintains a maximal temperature of 230 degrees Celsius. More generally between 0 airflow and a given airflow rate, the control circuitry may control the temperature of the capsule in proportion to the airflow rate, up to a maximum temperature. For some applications, the maximal temperature is between 200 degrees Celsius and 230 degrees Celsius. Beyond the given airflow rate, the control circuitry may maintain the capsule at the maximum temperature even if the airflow rate increases.

For some applications, a heating profile is applied as indicated by dashed curve in FIG. 10. For example, between 0 airflow rate percentage units and a first given airflow rate (e.g., 20 airflow rate percentage units, as shown in FIG. 10) the control circuitry may increase the temperature of the capsule in response to the increases in airflow rate, at a first rate. Between the first given airflow rate and a second given airflow rate (e.g., 70 airflow rate percentage units, as shown in FIG. 10), the control circuitry may increase the temperature of the capsule in response to the increases in airflow rate, at a second rate. For some applications, the second rate is lower than the first rate, i.e., at the second rate, the temperature increase in response to a given rise in airflow rate is less than the temperature increase that is applied in response to the same airflow rate rise, at the first rate. For some applications, beyond the second given airflow rate, the capsule is maintained at a given maximum temperature (e.g., a temperature of 230 degrees Celsius), even if the airflow rate increases.

As described hereinabove, for some applications, a heating profile is applied as indicated by dotted curve in FIG. 10. For such applications, in response to an increase in the airflow rate, the temperature to which the capsule is heated by the control circuitry is reduced.

Figure 11:
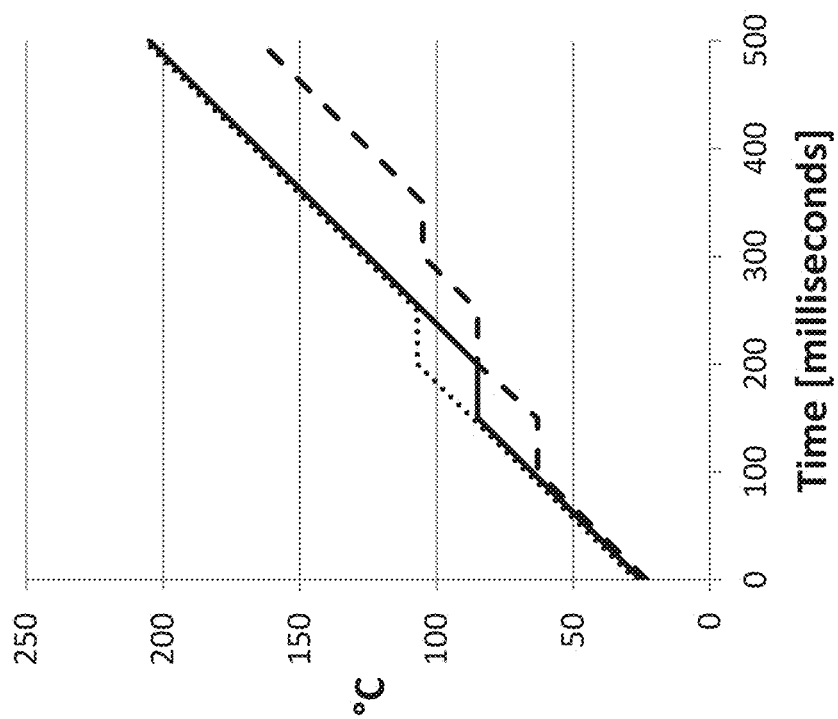
FIG. 11 is a graph illustrating heating curves of capsules containing phase-change materials with different phase-change temperatures, in accordance with an example embodiment.

Reference is now made to FIG. 11, which is a graph illustrating the heating curves of capsules that include phase-change materials, in accordance with some applications. As described hereinabove, for some applications, in order to enable the identification of the capsule type, use is made of the vaporizing unit's built-in temperature sensor, in combination with phase-change materials that are configured to have respective phase-change temperatures being included within respective capsule types.

The solid curve in FIG. 11 represents the heating curve of a capsule that includes or is thermally coupled to a phase-change material with a phase-change temperature of 85 degrees Celsius. As shown, when applying heat at a relatively constant power to the capsule, the temperature of the capsule rises in proportion with the heating power that is applied. When reaching the phase-change material's phase-change temperature of 85 degrees Celsius (at 150 milliseconds), a relatively large amount of energy in the form of latent heat is accumulated by the phase-change material at a relatively constant temperature, resulting in a detectable pause in the temperature increase of the capsule. For some applications, by detecting the temperature level at which the temporary pause in the temperature increase occurs, the control circuitry classifies the capsule as being a given type of capsule and adjusts the heating profile and/or other relevant functions accordingly. At a certain point in time, when the phase-change material has undergone its phase change, the temperature of the capsule continues to rise due to the applied heat energy, as seen on the solid curve of FIG. 11 after 200 milliseconds.

The dotted curve in FIG. 11 represents the heating curve of a capsule that includes or is thermally coupled to a phase-change material with a phase-change transition temperature of 105 degrees Celsius. The heating curve of the capsule is generally similar to that described with reference to the solid curve, but the temperature level at which the temporary pause in the temperature increase occurs is at a higher temperature of 105 degrees Celsius.

The dashed curve in FIG. 11 represents the heating curve of a capsule that includes or is thermally coupled to a combination of a plurality of different phase-change materials, in accordance with some applications. For some applications, the phase-change materials are mixed with each other, or are thermally coupled to each other without being mixed. The dashed curve of FIG. 11 shows an example in which three phase-change materials are used, the materials having phase-change transition temperatures of 65, 85, and 105 degrees Celsius. The heating curve of the capsule is generally similar to that described with reference to the solid curve, but due to the use of phase-change materials with three different phase-change transition temperatures, the heating curve will include three pauses in the temperature increase, each one due to its respective phase-change material reaching its phase changing temperature. By detecting the presence of a pause in temperature increase, information regarding the type of capsule is coded into the capsule and read by the control circuitry without necessarily requiring the use of a dedicated sensor within vaporizing unit 21, in addition to temperature sensor 35. In this manner, the use of a combination of phase-change materials, each with a different phase changing transition temperature, facilitates a coding method, which is used by the control circuitry for identification of the heated substance.

For some applications, the capsules are used with a phase-change temperature of the phase-change material is higher than 50 degrees Celsius and/or lower than 150 degrees Celsius, e.g., 50 to 150 degrees Celsius, or 80 to 120 degrees Celsius. For some applications, the phase-change material is thermally coupled to the plant material. For example, the phase-change material may be mixed with the plant material. For some applications, sheets of the phase-change material partially or fully cover the plant material.

Reference is now made to FIG. 12A, which is a graph illustrating respective techniques for heating plant material using a vaporizer, such as vaporizing unit 21, in accordance with some applications. The x-axis of the graph indicates time (measured in arbitrary time units), and the y-axis indicates the temperature (measured in degrees Celsius) of a capsule that contains a plant material (and therefore indicates the temperature of the plant material within the capsule), as described herein.

As described hereinabove, for some applications, the control circuitry controls a vaporizer (such as vaporizing unit 21) to vaporize one or more compounds within *cannabis*. *Cannabis* may have a vaporization temperature of 180 degrees Celsius, and may begin to become pyrolyzed at 220 degrees Celsius. Therefore, it may be desirable to heat the *cannabis* to a temperature of between 190 degrees Celsius and 210 degrees Celsius. The upper and lower boundaries of the desired temperature range to which to heat *cannabis* are denoted on the graph of FIG. 12A, by the two solid horizontal lines at 190 degrees Celsius and 210 degrees Celsius. Furthermore, it may be desirable not to heat the *cannabis* to a temperature that is greater than the described temperature, in order to reduce or prevent pyrolysis of the *cannabis*. When the vaporizer is used with plant materials other than *cannabis* (e.g., tobacco), similar considerations may be applicable, although the desired temperature to which the plant material should be heated will vary depending on the characteristics of the plant material that is being used with the vaporizer.

One possible way of heating the plant material to the desired temperature is via gradual heating, as denoted by the dashed diagonal line, which shows the plant material being heated to the desired temperature over a period of more than 8 time units. Another possible way to heat the plant material is via rapid heating, as denoted by the dotted curve in FIG. 12A. If the plant material is heated relatively rapidly, then initially there may be an overshoot in the temperature to which the plant material is heated. For example, this may be because there is a time lag between when the plant material reaches the desired temperature and when the control circuitry detects that the desired temperature has been reached and discontinues a further temperature increase of the plant material in response to the detected temperature. This is indicated in FIG. 12A, which shows that the dotted curve initially rises above 220 degrees Celsius, before plateauing within the desired temperature range. Due to the overshooting, some of the plant material may become pyrolyzed.

In accordance with some applications, a two-stage heating process is applied to material within a vaporizer, e.g., as indicated by the solid curve shown in FIG. 12A. In response to receiving a first input at the vaporizer (e.g., in response to the pressing of an ON switch on the vaporizer), the control circuitry of the vaporizer may initiate a first heating step. The first heating step may be a rapid heating step (e.g., a heating step in which the capsule that contains the plant material is heated at a rate of more than 50 degrees Celsius per second, or more than 100 degrees Celsius per second). Furthermore, the control circuitry of the vaporizer may be configured to terminate the first heating step, thereby discontinuing a further temperature increase of the capsule, in response to detecting that the temperature of the capsule (which is indicative of the temperature of the plant material) has reached a first temperature. The first temperature may be less than 95 percent, e.g., less than 90 percent, or less than 80 percent, of the vaporization temperature of the plant material. For example, when the vaporizer is used to vaporize *cannabis*, the control circuitry of the vaporizer may be configured to discontinue a further temperature increase of the capsule, in response to detecting that the temperature of the capsule has reached a first temperature that is less than 170 degrees Celsius (e.g., less than 160 degrees Celsius), e.g., a temperature that is between 140 and 170 degrees Celsius, or between 150 and 160 degrees Celsius.

By configuring the control circuitry to terminate the first, rapid heating stage as described above, even if there is overshoot, and the temperature of the capsule rises above the temperature at which the first heating stage was programmed to be terminated, the temperature of the capsule may be adequately controlled so as to not rise above the pyrolysis temperature of the plant material. For example, as shown in FIG. 12A, the control circuitry has been configured to discontinue a further temperature increase of the capsule in response to detecting that the temperature of the capsule has reached approximately 160 degrees Celsius. Initially (at approximately 1 time unit), there is an overshoot, and the temperature of the capsule reaches approximately 180 degrees Celsius. However, the temperature of the capsule then reaches a plateau of approximately 160 degrees Celsius, at about 2 time units. For some applications, the control circuitry of the vaporizer generates an output to indicate that the first stage of the heating has terminated. For example, the control circuitry may illuminate an indicator light, may cause the vaporizer to vibrate, and/or may emit an audio signal (e.g., a beep).

Subsequently, in response to a second input to the vaporizer, the control circuitry of the vaporizer initiates a second heating step (shown, on the solid curve in FIG. 12A, to begin at approximately 4 time units). Between the end of the first stage of the heating process and the initiation of the second stage of the heating process, the control circuitry may maintain the temperature of the capsule at the first temperature. For some applications, the second stage of the heating is initiated automatically in response to the inhalation of air from the vaporizer as the second input. Alternatively, the second stage of the heating process may be initiated in response to a different second input (e.g., the pressing of the ON button a second time). Furthermore, alternatively, the second stage of the heating process may be initiated automatically after the first stage of heating is complete, and an indication (such as an indicator light, a vibration, and/or an audio signal (e.g., a beep)) may be generated to indicate that the target temperature for the second heating stage has been reached.

During the second heating step, the control circuitry may heat the capsule at a slower rate than during the first stage of the heating process. For example, during the second stage of the heating process, the meshes of the capsules of the vaporizer may be heated at a rate of less than 50 degrees Celsius per second, e.g., less than 40 degrees Celsius per second. As shown in FIG. 12A, during the second stage of the heating process (from 4 time units to 6 time units) the capsule is heated from approximately 160 degrees Celsius to 200 degrees Celsius.

In the second stage of the heating process, the control circuitry is configured to discontinue a further temperature increase of the capsule in response to detecting that the temperature of the capsule is between the vaporization temperature of the plant material and the pyrolysis temperature of the plant material. For example, when the vaporizer is used to vaporize *cannabis*, the control circuitry of the vaporizer is configured to discontinue a further temperature increase of the capsule, in response to detecting that the temperature of the capsule has reached a second temperature that is more than 180 degrees Celsius (e.g., more than 190 degrees Celsius), and/or less than 220 degrees Celsius (e.g., less than 210 degrees Celsius), e.g., a temperature that is between 180 and 220 degrees Celsius, or between 190 and 210 degrees Celsius.

In a non-limiting embodiment, the control circuitry may be configured to place the vaporizer in standby mode if a subsequent second input (e.g., a draw or inhalation) is not detected within a period of time after the previous second input.

For some applications, by performing the heating in the two-stage process described hereinabove, one or more of the following results are achieved:

1) By terminating the first (rapid) stage of the heating in response to the temperature of the capsule reaching less than 95 percent of the vaporization temperature, even if the heating overshoots, the plant material is not pyrolyzed, since the plant material is not heated to a temperature that is greater than the pyrolysis temperature.
2) Since the second stage of the heating is performed slowly, there is negligible overshooting in the second stage of the heating process, and therefore the plant material does not get pyrolyzed in the second stage of the heating process.
3) Since, during the first stage of the heating, the plant material has already been heated to a temperature that is relatively close the vaporization temperature, even though the second stage of the heating is slow, the time that is required to heat the plant material to the vaporization temperature, from the initiation of the second heating stage, is relatively short (e.g., less than two seconds).
4) Due to low heat conduction of the plant material, if the plant material is heated rapidly, this can give rise to non-uniform heating of the plant material. This can cause portions of the plant material that are near to the heating element(s) (e.g., the electrode(s)) to be pyrolyzed, and/or portions of the plant material that are further from the heating element(s) not to be vaporized. By withholding a further heating of the plant material after the first temperature has been reached, and until the second input is received, heat is able to dissipate through the plant material (during the interim period between the first and second heating stages) before any portion of the plant material has been heated to the vaporization temperature. Furthermore, since the temperature increase during the second stage is relatively small, the temperature increase is able to dissipate through the plant material relatively quickly. Thus, relatively uniform heating of the plant material is achieved, such that most of the compound(s) within the plant material is vaporized, while there is substantially no pyrolysis of the plant material.

For some applications, the draw or inhalation from the vaporizer is automatically detected by the control circuitry. In a non-limiting embodiment combinable with any previous or forgoing embodiment, the control circuitry includes any well-known puff sensor to detect draw or inhalation.

After the first stage of the heating, there may be a relatively large difference between the ambient temperature and the temperature of the capsule that contains the plant material. As described hereinabove, between the end of the first stage and the initiation of the second stage of the heating process, the control circuitry maintains the temperature of the capsule at the first temperature. Since there is a relatively large difference between the ambient temperature and the first temperature of the capsule, the energy that is required to maintain the capsule (and the plant material therein) at a constant temperature is greater when there is a draw or inhalation. Therefore, for some applications, the control circuitry detects that there is a draw or inhalation from the vaporizer by detecting the amount of energy required to maintain the temperature of the capsule (and the material therein) constant. In an example embodiment, the control circuitry detects a draw or inhalation when the amount of energy needed to maintain the temperature of the capsule is greater than a threshold amount of energy. The threshold may be a design parameter determined through empirical study. For example, the control circuitry may detect variations in the duty cycle that is used to heat the capsule (and the plant material therein). In such an instance, the control circuitry detects a draw or inhalation when the detected duty cycle is determined to be greater than a threshold duty cycle. The threshold may be a design parameter determined through empirical study. Alternatively or additionally, the control circuitry may automatically detect that there is inhaling from the vaporizer by directly detecting the temperature of the capsule. Since, after the first stage of the heating, there is a relatively large difference between the ambient temperature and the temperature of the capsule, airflow through the capsule may cause a measurable change in the temperature of the capsule. If this change exceeds a threshold, then draw or inhalation is detected. The threshold may be a design parameter determined through empirical study. As described hereinabove, for some applications, the second stage of the heating process is initiated automatically in response to detecting inhalation from the vaporizer.

For some applications, in response to detecting that no inhalation has occurred over a given time period (e.g., a time period of between 0.5 seconds and 3 seconds), the temperature of the capsule is reduced to below the vaporization temperature of the plant material. For example, during use of the vaporizer, a subject may stop inhaling for a given time period. By reducing the temperature to below the vaporization temperature, wastage of the compound during this period is reduced, such that the prescribed dosage of the compound can be received.

As indicated by the solid curve in FIG. 12A, between approximately 8 time units and 10 time units the control circuitry causes the temperature of the capsule to be lowered to below the vaporization temperature. This may be performed in response to detecting that no inhalation has occurred over a given time period (as described hereinabove), and/or in response to a subject input (e.g., in response to the pressing of a button). From approximately 10 time units to 13 time units, the capsule is heated back to the vaporization temperature. This may be performed in response to detecting that inhalation has resumed and/or in response to a subject input (e.g., in response to the pressing of a button). Between approximately 15 time units and 17 time units the control circuitry again causes the temperature of the capsule to be lowered to below the vaporization temperature. This may be performed in response to detecting that no inhalation has occurred over a given time period, and/or in response to an input (e.g., in response to the pressing of a button).

Figure 12B:
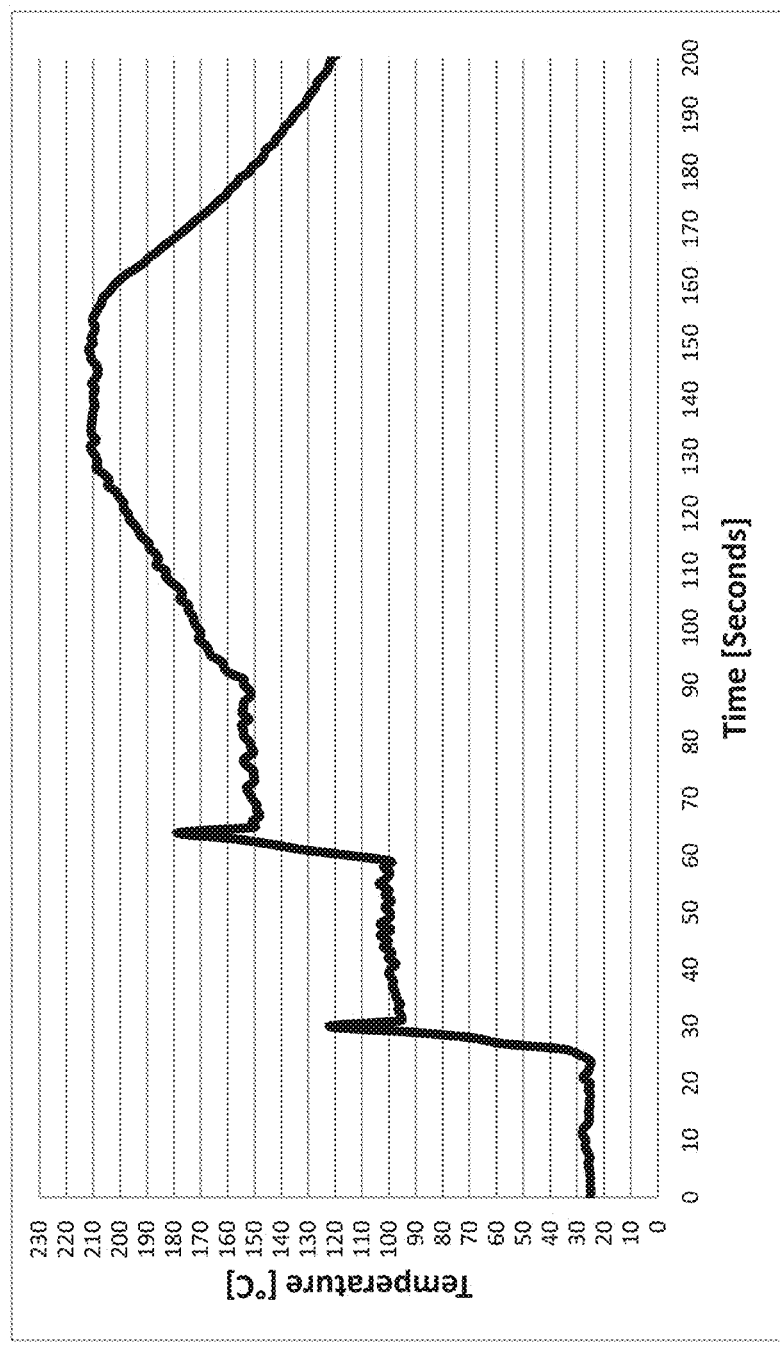
FIG. 12B is a graph illustrating a 3-stage technique for heating a material using a vaporizer, in accordance with an example embodiment.

Reference is now made to FIG. 12B, which is a graph illustrating a technique for heating plant material using a vaporizer, in accordance with some applications. For some applications, a three-stage (or three-step) heating process is applied to plant material within a vaporizer. The second two stages of the heating process are generally similar to those described with reference to the solid curve shown in FIG. 12A. (With respect to FIG. 12B, these stages are referred to, respectively, as the second and third heating stages.) For some applications, an additional, initial stage of heating is applied, in order to remove humidity from the plant material, as shown in FIG. 12B.

For example, when the vaporizer is being used with *cannabis*, the vaporizer may apply the following three heating stages to the *cannabis*:

1) Heating to a first temperature that may be more than 90 degrees Celsius (e.g., more than 100 degrees Celsius) and/or less than 120 degrees Celsius (e.g., less than 110 degrees Celsius, e.g., between 90 degrees Celsius and 120 degrees Celsius (or between 100 and 110 degrees Celsius). For some applications, the plant material is maintained at approximately the first temperature (e.g., the first temperature plus/minus 5 degrees Celsius) for a given time period, for example, in order to remove moisture from the plant material prior to vaporization of a compound during subsequent heating. In FIG. 12B, the first heating stage is shown as being initiated at approximately 28 seconds. Initially, the temperature overshoots, but then is shown to plateau at between approximately 95 degrees Celsius and 105 degrees Celsius. For some applications, the plant material is maintained at approximately the first temperature for a time period of more than 5 seconds, e.g., between 5 and 60 seconds (e.g., approximately 25 seconds, as shown in FIG. 12B). The first heating step may be a rapid heating step (e.g., a heating step in which the capsule that contains the plant material is heated at a rate of more than 50 degrees Celsius per second, or more than 100 degrees Celsius per second). In some methods, *cannabis* is heated to a temperature of 90° to 110° C. for 5 to 15 seconds prior to further heating. Furthermore, the control circuitry of the vaporizer may be configured to discontinue a further temperature increase of the capsule, in response to detecting that the temperature of the capsule (which is indicative of the temperature of the plant material) has reached the first temperature. In some applications, the heating is performed for such time as to reduce the moisture in a material to a desired level. For example, the heating may be performed to reduce the moisture within a plant material to about 10 to 40% by weight of the plant material (e.g., 10 to 15% by weight of the plant material).

2) Heating to a second temperature that may be more than 140 degrees Celsius (e.g., more than 150 degrees Celsius), and/or less than 170 degrees Celsius (e.g., less than 160 degrees Celsius), e.g., between 140 and 170 degrees Celsius (or between 150 and 160 degrees Celsius). This corresponds to the first heating stage shown by the solid curve in FIG. 12A. In FIG. 12B, this stage is shown as being initiated at approximately 63 seconds. Initially, the temperature overshoots, but then is shown to plateau at between approximately 145 degrees Celsius and 155 degrees Celsius. For some applications, the plant material is maintained at approximately the second temperature (e.g., the second temperature plus/minus 5 degrees Celsius) for a given time period. For example, the plant material may be maintained at the second temperature for a time period of more than 5 seconds, e.g., between 5 seconds and 7 minutes.

3) Heating to a third temperature that is more than 180 degrees Celsius (e.g., more than 190 degrees Celsius), and/or less than 220 degrees Celsius (e.g., less than 210 degrees Celsius), e.g., a temperature that is between 180 and 220 degrees Celsius, or between 190 and 210 degrees Celsius. As shown in FIG. 12B, the third stage of heating is initiated at approximately 90 seconds and continues until approximately 155 seconds.

In some applications, methods comprise heating a plant material to alter the chemical composition of the plant material prior to vaporization. Such alteration may be by chemical reaction, by altering relative levels of compounds in the material, or both. In some applications, heating causes, initiates, or accelerates a chemical reaction to convert a precursor to a compound, which is then vaporized from the material by subsequent heating. Such methods may comprise producing a plant material vapor from a plant material comprising a temperature-sensitive component at a first concentration, by heating a volume of the plant material to a first temperature to form a heated volume of the plant material having a second concentration of the temperature-sensitive component. In some methods, the first concentration is greater than the second concentration. In other methods, the first concentration is less than the second concentration. The method may additionally include heating the heated volume of plant material to a second temperature to form the plant material vapor comprising the temperature-sensitive component. The temperature-sensitive component may be converted to a second component during the heating to the first temperature. As a result, the plant material vapor may further comprise the second component.

For example, methods for producing a dose of plant material vapor, from a mass of plant material comprising an initial quantity of a compound and an initial quantity of a precursor of the compound, comprise converting the precursor to the compound by heating the mass of the plant material to a first temperature of 140° to 160° C. for 5 to 15 seconds to obtain a converted mass of plant material containing a decreased quantity of the precursor and an increased quantity of the compound. The method may additionally comprise vaporizing the compound in the converted mass by heating the converted mass to a second temperature of 190° to 200° C. for 2 to 5 seconds to generate the dose of plant material vapor.

In some applications, the heating may change an organoleptic profile (e.g., flavor profile) of the plant material. The plant material may be tobacco. In another instance, the plant material may be *cannabis*. In some applications, the heating may decarboxylate a precursor in the plant material, such as *cannabis*, to form a compound, as further described below.

In some applications, the present technology provides methods for providing pharmacologic benefits by administering a vapor created using a device as described herein, such as by heating a plant material comprising cannabinoids. Cannabinoids interact with different receptors in the body to produce a wide range of effects. As a result, cannabinoids have been used for a variety of medicinal purposes. Notable cannabinoids include tetrahydrocannabinol (THC) and cannabidiol (CBD). Tetrahydrocannabinolic acid (THCA) is a precursor of tetrahydrocannabinol (THC), while cannabidiolic acid (CBDA) is precursor of cannabidiol (CBD). Tetrahydrocannabinolic acid (THCA) and cannabidiolic acid (CBDA) may be converted to tetrahydrocannabinol (THC) and cannabidiol (CBD), respectively, and administered in accordance with the devices and associated methods discussed herein.

Exemplary methods of treatment provided by the present technology include treatment of pain management, appetite stimulation, treatment of nausea and vomiting, treatment of glaucoma, treatment of opioid and other drug dependency and withdrawal, treatment of epilepsy, treatment of asthma, and treatment of psychiatric disorders. In particular, the present technology provides methods for the treatment of pain in a human or other animal subject, comprising administering to the subject a vapor produced by heating a cannabinoid-containing material using a device as described herein. Plant material may be obtained from any suitable *cannabis* species or mixtures thereof. For example, in some applications, the plant material is a mixture of *Cannabis sativa* and *Cannabis* indica, such as a mixture of about 70% *sativa* and about 30% indica. In some applications, plant material may comprise from 15 to 30%, or from 20-22% THC.

Treatment of pain may include prevention, reduction, or elimination of pain due a variety of diseases and other disorder in hard and soft tissues. Such disorders may be associated with acute or chronic disorders, and may be nociceptive, neuropathic, or inflammatory. For example, pain treated by methods herein may be associated with such disorders as rheumatoid arthritis, osteoarthritis, cancer, visceral pain, neuropathy, multiple sclerosis, traumatic injury, surgical procedures, and dental procedures. In some applications, methods are for the treatment of moderate pain (Visual Analogue Scale (VAS) 4-6) or severe pain (VAS 7-10).

Accordingly, for some applications comprising multi-step heating as described above, the plant material is heated to a temperature sufficient to decarboxylate a compound in the plant material prior to vaporizing the material. For example, *cannabis* may be maintained at the second temperature for a time period that is sufficient to cause decarboxylation, i.e., to convert Tetrahydrocannabinolic Acid (THCA) that is present in the *cannabis* to Tetrahydrocannabinol (THC), and/or to convert Cannabidiolic Acid (CBDA) to Cannabidiol (CBD). For some applications, maintaining the plant material at the second temperature causes the decarboxylation of the *cannabis* in accordance with an article by Dussy, et al., entitled "Isolation of Delta9-THCA-A from hemp and analytical aspects concerning the determination of Delta9-THC in *cannabis* products (Forensic Sci. Int. 2005 Apr. 20; 149(1):3-10), the entire disclosure of which is incorporated herein by reference, and/or an article by Veress, et al., entitled "Determination of cannabinoid acids by high-performance liquid chromatography of their neutral derivatives formed by thermal decarboxylation: I. Study of the decarboxylation process in open reactors" (Journal of Chromatography A 520:339-347, November 1990), the entire disclosure of which is incorporated herein by reference. For example, FIG. 12B shows the plant material being maintained at approximately the second temperature for approximately 25 seconds.

The second heating step may be a rapid heating step (e.g., a heating step in which the capsule that contains the plant material is heated at a rate of more than 50 degrees Celsius per second, or more than 100 degrees Celsius per second). Furthermore, the control circuitry of the vaporizer may be configured to discontinue a further temperature increase of the capsule, in response to detecting that the temperature of the capsule (which is indicative of the temperature of the plant material) has reached the second temperature.

As described hereinabove, for some applications, the third stage of the heating (which corresponds to the second heating stage shown by the solid curve in FIG. 12A) is initiated automatically in response to inhalation of air from the vaporizer. Alternatively, the third stage of the heating process may be initiated in response to a different input (e.g., the pressing of the ON button a second time). Furthermore, alternatively, the third stage of the heating process may be initiated automatically after the second stage of heating is complete, and an indication (such as an indicator light, a vibration, and/or an audio signal (e.g., a beep)) may be generated to indicate that the target temperature for the third heating stage has been reached. During the third heating stage, the control circuitry may heat the capsule at a slower rate than during the first and second stages of the heating process. For example, during the third stage of the heating process, the meshes of the capsules of the vaporizer may be heated at a rate of less than 50 degrees Celsius per second, e.g., less than 40 degrees Celsius per second. In the third stage of the heating process, the control circuitry is configured to discontinue a further temperature increase of the capsule in response to detecting that the temperature of the capsule is between the vaporization temperature of the plant material and the pyrolysis temperature of the plant material. For example, when the vaporizer is used to vaporize *cannabis*, the control circuitry of the vaporizer is configured to discontinue a further temperature increase of the capsule, in response to detecting that the temperature of the capsule has reached a third temperature that is more than 180 degrees Celsius (e.g., more than 190 degrees Celsius), and/or less than 220 degrees Celsius (e.g., less than 210 degrees Celsius), e.g., a temperature that is between 180 and 220 degrees Celsius, or between 190 and 210 degrees Celsius.

It is noted that, although the three-stage heating process has been described primarily with respect to using *cannabis* as the plant material, the scope of the present disclosure includes applying a three-stage heating process to other plant materials (e.g., tobacco), mutatis mutandis. The temperatures and time periods that are used in the three-stage heating process when applied to plant materials other than *cannabis* will vary, in accordance with the characteristic vaporization temperatures, pyrolysis temperatures, and other chemical characteristics of the plant materials.

As discussed above, cannabinoids may be administered for a variety of medical situations, such as to treat pain. Thus, for example, a method of treating pain in a human or animal subject may comprise heating a volume of THC/THCA-containing *cannabis*, e.g., to a first temperature of 140° to 160° C. for 5 to 15 seconds to form a heated volume of the *cannabis*. While the volume of *cannabis* may have some tetrahydrocannabinol (THC) already present, the heating to the first temperature will convert the tetrahydrocannabinolic acid (THCA) in the volume of *cannabis* into additional tetrahydrocannabinol (THC).

Similarly, a method of treating pain in a human or animal subject may comprise heating a volume of CBD/CBDA-containing *cannabis* e.g., to a first temperature of 140° to 160° C. for 5 to 15 seconds to form a heated volume of the *cannabis*. While the volume of *cannabis* may have some cannabidiol (CBD) already present, the heating to the first temperature will convert the cannabidiolic acid (CBDA) in the volume of *cannabis* into additional cannabidiol (CBD).

The method may additionally comprise heating the heated volume of the *cannabis* to a second temperature of 190° to 200° C. for 2 to 5 seconds to form a dose of vapor comprising the compound (e.g., THC or CBD). The compound in the dose of vapor will include the compound already present in the volume of *cannabis* along with the additional quantity formed as a result of the heating to the first temperature. It should be understood that the heating to the second temperature may be performed from the first temperature or from a lower temperature after the heated volume has cooled to below the first temperature (e.g., cooled to an ambient temperature due to inactivity).

A method of treating pain in a human or animal subject may comprise decarboxylating a precursor in a mass of *cannabis* (the mass of *cannabis* containing an initial quantity of a compound and an initial quantity of the precursor) by heating the mass of *cannabis* to a first temperature of 140° to 160° C. for 5 to 15 seconds to obtain a converted mass of *cannabis* containing a decreased quantity of the precursor and an increased quantity of the compound. The method may additionally comprise vaporizing the compound in the converted mass by heating the converted mass to a second temperature of 190° to 200° C. for 2 to 5 seconds to generate a dose of vapor comprising the compound. The method may also comprise administering the dose of vapor to the subject. The method may further comprise reducing the moisture in the mass of *cannabis* at a preliminary temperature, as described above, such as from 90 to 110° C. for 5 to 15 seconds prior to the decarboxylating. The compound may be tetrahydrocannabinol (THC) and the precursor may be tetrahydrocannabinolic acid (THCA). Alternatively or in addition, the compound may be cannabidiol (CBD) and the precursor may be cannabidiolic acid (CBDA).

Methods of treatment also comprise administering the vapor to a human or other animal subject in need of the treatment. In some applications, methods comprise administering one or more doses of vapor. Such doses may comprise one or more inhalations (or "puffs") from a vapor device as described herein. A dose preferably comprises a safe and effective amount of one or more compounds, such as THC or CBD. A "safe and effective" amount of a compound is an amount that is sufficient to have the desired therapeutic effect in the human or animal subject (e.g., treatment of pain), without undue adverse side effects (such as toxicity, irritation, or allergic response), commensurate with a reasonable benefit/risk ratio when used in the manner of this technology. The specific safe and effective amount of the compound will vary with such factors as the particular condition being treated, the physical condition of the patient, the nature of concurrent therapy (if any), the specific compound used, and the desired dosage regimen. In some applications comprising the vaporization of *cannabis* plant material, the dose is sufficient to effect pain relief, while creating little or no cognitive impairment. In particular, for a given subject, there is a minimum dose of vapor (lower threshold) needed for treatment (e.g., pain relief). At the same time, there is a higher dose of vapor (upper threshold) which will have a psychoactive effect on the subject. Accordingly, in an example embodiment, the dose of vapor during treatment is tailored so as to be above the lower threshold but below the upper threshold. These thresholds may be design parameters determined through empirical study.

In some applications, methods are performed on a THC-containing *cannabis* plant material so as to allow the vaporization and administration of at least 1 mg of tetrahydrocannabinol (THC) per 25 mg of *cannabis* plant material. For example, the methods may be performed to allow the vaporization and administration of 2 mg to 7.5 mg of THC per 25 mg of *cannabis* plant material (e.g., 5 mg of THC per 25 mg of *cannabis* plant material). The method may be controlled so as to allow the vaporization and administration of the THC to be within ±5% of a target dose for the volume of *cannabis* (e.g., within ±3% of a target dose for the volume of *cannabis*). In a non-limiting embodiment, the vaporization and administration of the THC may be within ±0.1 mg of a 2 mg target dose for the volume of *cannabis*. The dose of vapor may comprise from 1 mg to 7.5 mg of THC (e.g., 2 mg to 5 mg of THC). It should be understood that the dose of vapor may be administered from the vaporizing device via one or more draws depending on the length/extent of each draw (e.g., via a fewer number of longer draws or a greater number of shorter draws). In another instance, the dose of vapor may comprise the tetrahydrocannabinol (THC) and tetrahydrocannabinolic acid (THCA) at a THC:THCA ratio of at least 1:50. For example, the THC:THCA ratio may be at least 1:2 (e.g., 1:1). Furthermore, at least 50% of the THCA in the THC/THCA-containing *cannabis* may be converted to THC. For example, at least 87% of the THCA in the *cannabis* may be converted to THC.

In some applications, methods are performed using a CBD-containing *cannabis* plant material so as to allow the vaporization and administration of at least 1 mg of cannabidiol (CBD) per 25 mg of *cannabis* plant material. For example, the methods may be performed to allow the vaporization and administration of at least 2 mg to 7.5 mg of CBD per 25 mg of *cannabis* plant material (e.g., 5 mg of CBD per 25 mg of *cannabis* plant material). The method may also be controlled so as to allow the vaporization and administration of the CBD to be within ±5% of a target dose for the volume of *cannabis* (e.g., within ±3% of a target dose for the volume of *cannabis*). In a non-limiting embodiment, the vaporization and administration of the CBD to be within ±0.1 mg of a 2 mg target dose for the volume of *cannabis*. The dose of vapor may comprise from 1 mg to 7.5 mg of CBD (e.g., 2 mg to 5 mg of CBD). In another instance, the dose of vapor may comprise the cannabidiol (CBD) and cannabidiolic acid (CBDA) at a CBD:CBDA ratio of at least 1:50. For example, the CBD:CBDA ratio may be at least 1:2 (e.g., 1:1). Furthermore, at least 50% of the CBDA in the CBD/CBDA-containing *cannabis* may be converted to CBD. For example, at least 87% of the CBDA in the *cannabis* may be converted to CBD.

Figure 13A:
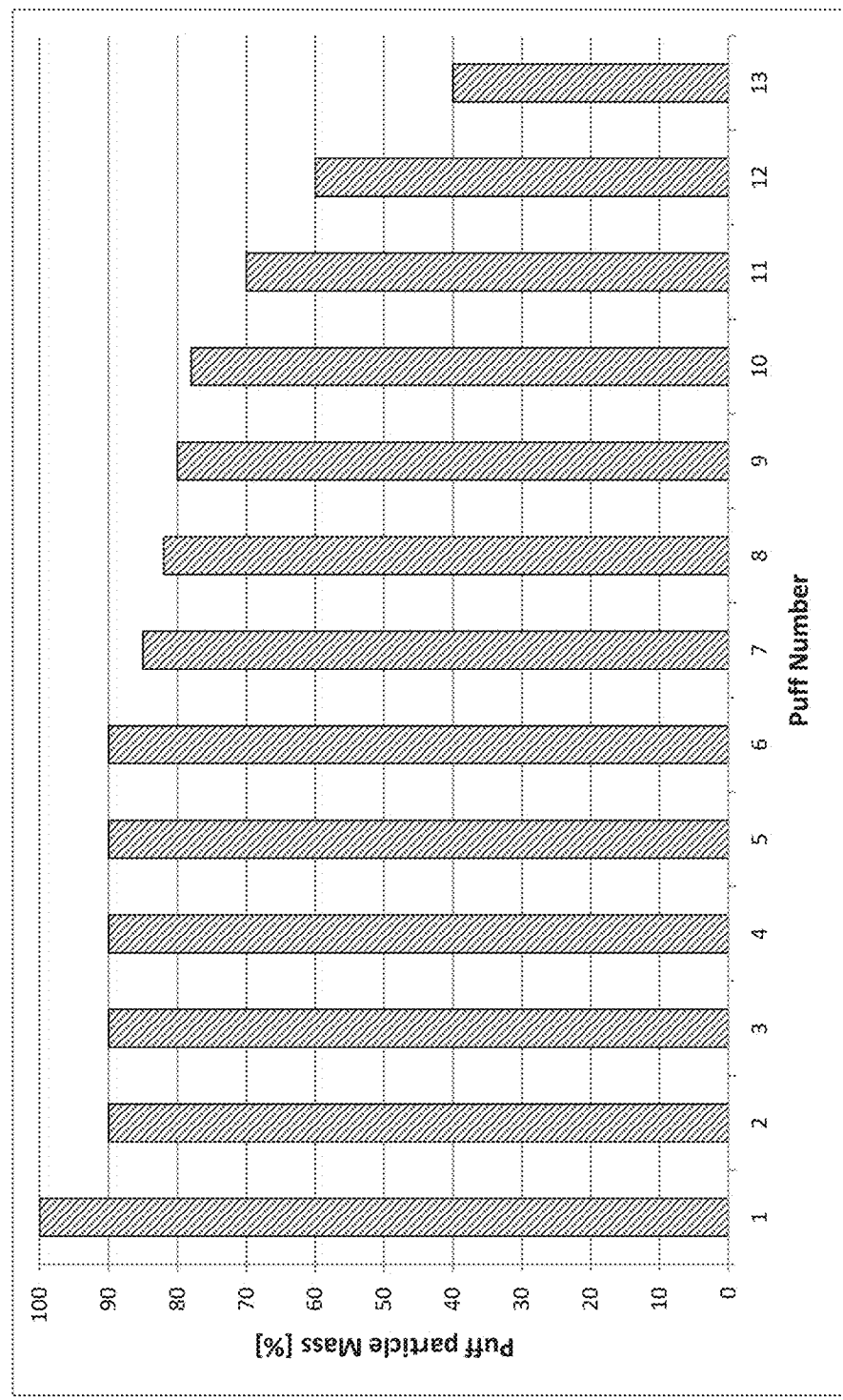
FIGS. 13A and 13B are bar charts showing the puff particle mass that is released with successive puffs of a vaporizer, in accordance with an example embodiment.
Figure 13B:
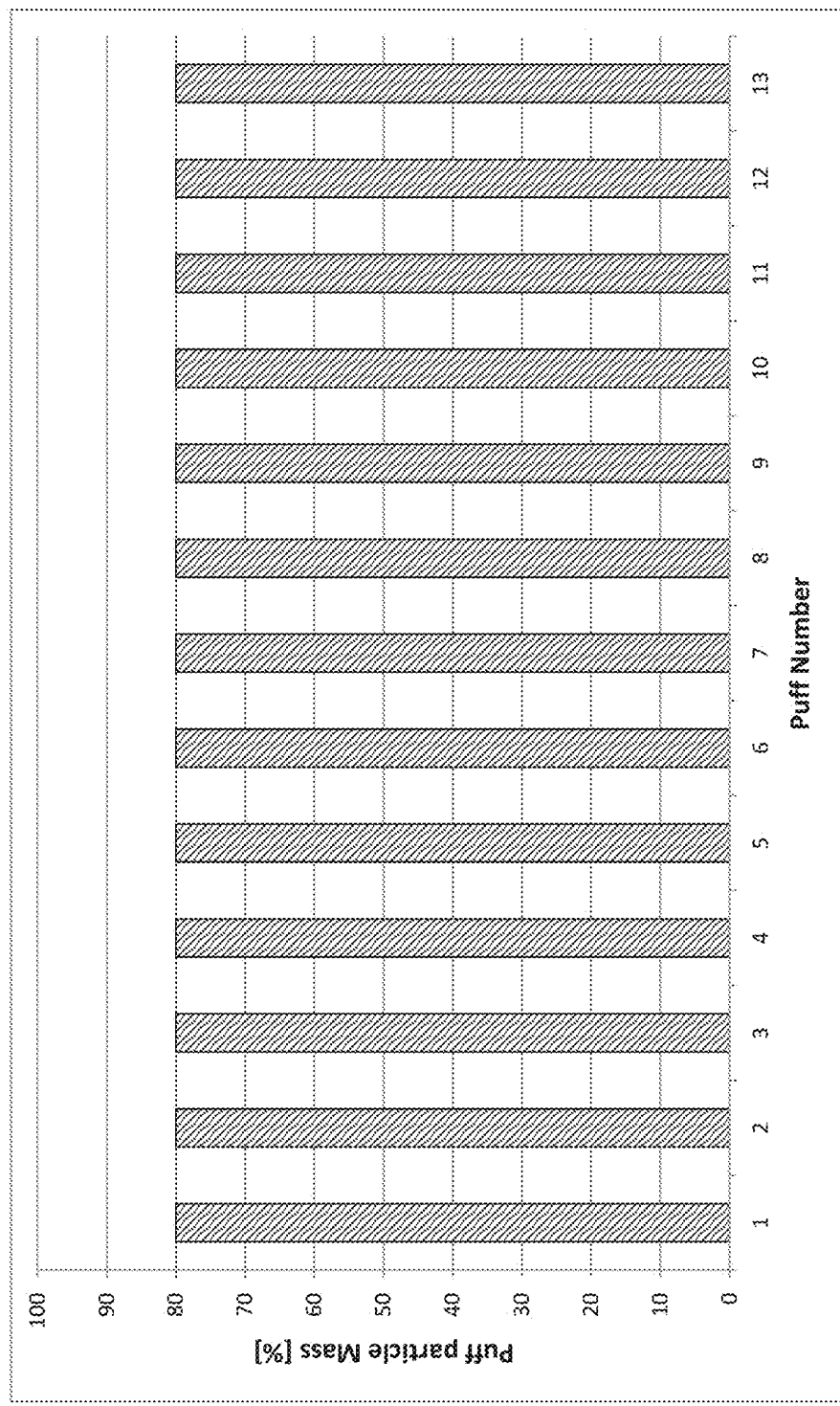

Reference is now made to FIGS. 13A and 13B, which are bar charts showing the puff particle mass (e.g., of a compound) that is released from plant material with respective, successive puffs of vaporizer, in accordance with some applications. The y-axis of the bar charts measures the puff particle mass of a compound that is released from the plant material as a percentage of a given arbitrary mass. The bar charts show the mass of a compound that is released from plant material during each of the puffs, assuming that the total airflow through the capsule during each of the puffs is the same as each other.

FIG. 13A shows an example of the mass of a compound that is released from plant material during each of the puffs, if the capsule is heated to the same temperature during each of the puffs. As shown, during successive puffs, the mass of the compound that is released from plant material during successive puffs decreases, because with each successive puff, more of the compound has already been released from the plant material, such that there is less of the compound available to be released.

As described hereinabove, for some applications, the control circuitry accounts for the amount of compound that has already been vaporized from the portion of the plant material that is currently being heated (which may, for example, be a portion of the plant material that is disposed inside a capsule). For example, in some cases, based on the rates of airflow and temperatures that have already been applied to the capsule that is currently being heated, the control circuitry may determine an amount of the compound that has already been vaporized. For some applications, the control circuitry determines the target temperature to which to heat the capsule, in response to the amount of the compound that has already been vaporized. For example, for a given airflow rate, the control circuitry may heat the capsule to a greater temperature, the greater the amount of the compound that has already been vaporized.

FIG. 13B shows an example of the mass of a compound that is released from a plant material during successive puffs, in accordance with such applications. As shown, the mass of the compound that is released from the plant material during successive puffs remains constant, because the control circuitry increases the temperature to which the plant material is heated, such as to account for the fact that, with each successive puff, more of the compound has already been released from the plant material. As a result of the control circuitry of the vaporizer accounting for the fact that, with each successive puff, more of the compound has already been released from the plant material, it is the case that, for any given inhalation airflow rate, there is no (or negligible) change in the strength, flavor, and/or mouthfullness of the vapors that are generated by the vaporizer between the beginning of the use of the portion of plant material (e.g., the capsule), and the end of use of the portion of plant material.

The scope of the present application also includes the apparatus and methods described in International Application No. PCT/IL2016/050293 (published as WO 2016/147188), filed Mar. 17, 2016, entitled "Vaporizer for vaporizing an active ingredient," which claims priority from and is a continuation-in-part of U.S. application Ser. No. 14/662,607 (published as US 2016/0271347), filed Mar. 19, 2015, entitled "Vaporizer for vaporizing an active ingredient," the entire disclosures of both of which are incorporated herein by reference.

Applications of the present technology are further illustrated through the following non-limiting example.

Example

A study was conducted to investigate the pharmacokinetics, efficacy, safety, and ease of use of a vaporizer device of the present technology for treating disorders in humans. Volunteers were recruited for participation in the study and met the following inclusion criteria: (a) age >30 and <70 years; (b) no known medical problems; and (c) if applicable, negative urine pregnancy test (β human chorionic gonadotropin pregnancy test). Exclusion criteria were the presence of (a) significant cardiac or pulmonary disease, (b) history of a psychotic or anxiety disorder, (c) pregnancy, pregnancy attempt or breastfeeding, (d) presence of a neuropathic or non-neuropathic pain disorder, (e) low systolic blood pressure, (>90 mm Hg) (f) diabetes (g) first degree family history of psychotic or anxiety disorder, (h) history of drug addiction, (i) history of drug misuse, (j) concurrent use the following drugs: rifampicin, rifabutin, carbamazepine, or phenobarbital, primidone, (k) using the following plants: *Hypericum perforatum*, troglitazone, (l) alcohol consumption up to 12 hours prior to the study, (m) abnormal parameters such as heart rate above 100 BPM, blood pressure below 90 mm Hg (systolic), saturation below 91 percent, (n) recreational *Cannabis* use up to 72 hours before the study, (o) any chronic use of drugs, and (q) age less than 30 or more than 70.

The study had a single-ascending dose design. The participants were divided into four dose related groups each group included 3 volunteers. After 3 successful training inhalations, each participant inhaled 3 seconds of a single dose. Dose groups were 10±0.1 mg, 15±0.1 mg, 20±0.1 mg, 25±0.1 mg of THC.

Blood samples were drawn immediately before and at 2, 3, 4, 10, 30 minutes after inhalation for monitoring of plasma levels of THC and its active metabolite $\Delta^9$ Carboxy-THC. The blood was collected in 13×75 mm purple-top Vacutainer tubes containing EDTA. Samples were kept on ice and centrifuged within 30 minutes. Plasma samples were aliquoted into 3.6-mL polypropylene Nunc cryotubes (Thomas Scientific, NJ, USA), stored frozen at −20° C., and analyzed within 6 weeks. The cannabinoid analysis was performed at Pactox (Pacific Toxicology Laboratories) Labs by multidimensional gas chromatography mass spectrometry method.

Adverse events were recorded at 5, 15, 30, 60, and 120 minutes post inhalation, along with those spontaneously reported by the participants. Adverse events were evaluated according to standardized criteria in terms of severity, frequency, duration, and relationship to study drug. Adverse events were graded using the NIH Division of AIDS table for scoring severity of adult adverse experiences.

Blood pressure, pulse rate, and oxygen saturation were also recorded at baseline, 30, 60, 90, and 120 minutes post inhalation. A cognitive test was conducted using the Short Blessed Test prior to the experiment at 30, 60 minutes after inhalation and at the end of the experiment.

The study device was as described above in connection with the figures and designed to vaporize up to 80 doses of processed *cannabis* flos, resulting in the pulmonary delivery of compounds. The inhaler consisted of a multi-dose cartridge, indication light, and power switch. The cartridge was preloaded with multiple pre-weighed 10.0±0.1 mg, 15.0±0.1 mg, 20.0±0.1 mg, and 25.0±0.1 mg doses of processed *cannabis* flos. The vaporization process was segmental and triggered by the volunteer pressing the operating button. The segmental evaporation process is aimed at turning THCA into THC[1] and is done by: (1) stage I—heating the material to 100° C. for 9 seconds; (2) stage II—heating the material to 150° C. for 9 seconds; (3) stage III—heating the material to 190° C. to 200° C. (evaporation temperature) for the 3 seconds of inhalation. The transition to the next dose/inhalation is performed by using a mechanical rotation wheel. The device engages automatic thermal control that ensures a complete, high-efficiency delivery of cannabinoid vapors to the lungs. The device allowed for "single inhalation" dose resolution, instantaneous administration, and required no preprocessing or any subject intervention other than the inhalation itself.

The *cannabis* flowers used in the study were of the Alaska strain provided by "Tikun Olam." This strain is a hybrid of 70% *sativa* and 30% indica strains. This strain consists of 20-22% THC and 0% CBD. The processed *cannabis* flowers used in this study were tested for THC by modified gas-chromatography method without derivatization18 resulting in $\Delta^9$-THC content of 20.08%. The flowers were loaded into the inhaler so as to retain the natural *cannabis* compounds in their raw form. The study drug was provided preloaded into separate cartridges that delivered the appropriate dosages.

The primary outcome of the study was to characterize the inter-individual variability of $\Delta^9$-THC during the absorption phase. The secondary outcome included (a) monitoring adverse effects, (b) blood pressure, and heart rate; and (c) monitoring the response of single-ascending dose with the use of the study device. In addition, the influence of the use of the trial device on the cognitive status of the subject was assessed. A Short Blessed Test cognitive test[19] was used for the purpose of the trial.

The following parameters were directly derived from the study data: (1) each arm $\Delta^9$ Tetrahydrocannabinol (THC) peak concentration ($C_{max}$±SD); (2) Time to reach peak THC concentration ($T_{max}$±SD); and (3) 9-Carboxi THC. From the $\Delta^9$-THC to Time curve a plot was generated, and an area under the curve (AUC) was determined by a linear numerical trapezoidal non-compartmental analysis or the exact method. The results are shown as mean±SD unless otherwise specified.

During the current study 12 healthy volunteers were recruited for the experiment. Volunteer's basic data is depicted in Table 1, below.

TABLE 1

Volunteers' baseline characteristics

| Volunteer | A | B | C | D | E | F | G | H | I | J | K | L |
|---|---|---|---|---|---|---|---|---|---|---|---|---|
| Dose in mg | 10 | 10 | 10 | 15 | 15 | 15 | 20 | 20 | 25 | 20 | 25 | 25 |
| Gender | M | F | F | M | M | F | F | M | M | M | M | M |
| Age (Years) | 32 | 32 | 31 | 36 | 51 | 42 | 33 | 34 | 37 | 30 | 30 | 31 |
| Weight (Kg) | 67 | 59.4 | 60 | 68.4 | 69.5 | 55 | 53 | 63 | 75 | 72 | 68 | 90 |
| BMI | 26.2 | 21.8 | 20.3 | 22.9 | 21.5 | 21.5 | 22.1 | 19.4 | 21.2 | 22.5 | 21.5 | 26.9 |

BMI = Body Mass Index

Ascending doses of THC produced a linear increase in the maximum concentration with the same linear increase in the dimension of the AUC both with no significant change in the time needed to reach such concentration. See Table 2, below.

TABLE 2

Mean values for the different dosage groups

| | Group I<br>10 ± 0.1 mg | Group II<br>15 ± 0.1 mg | Group III<br>20 ± 0.1 mg | Group IV<br>25 ± 0.1 mg |
|---|---|---|---|---|
| $\Delta^9$-THC $C_{max}$ (ng/mL) | 35.43 ± 5.97 | 51.47 ± 13.79 | 72.37 ± 15.93 | 88.63 ± 14.75 |
| $AUC_{0-\infty}$ (ng min/mL) | 441.59 ± 88.49 | 624 ± 123.56 | 698.35 ± 174.98 | 971.36 ± 310.4 |
| $T_{max}$ (min) | 3.666 ± 0.471 | 3.333 ± 0.471 | 2.666 ± 0.942 | 3 ± 0.816 |

Figure 14:
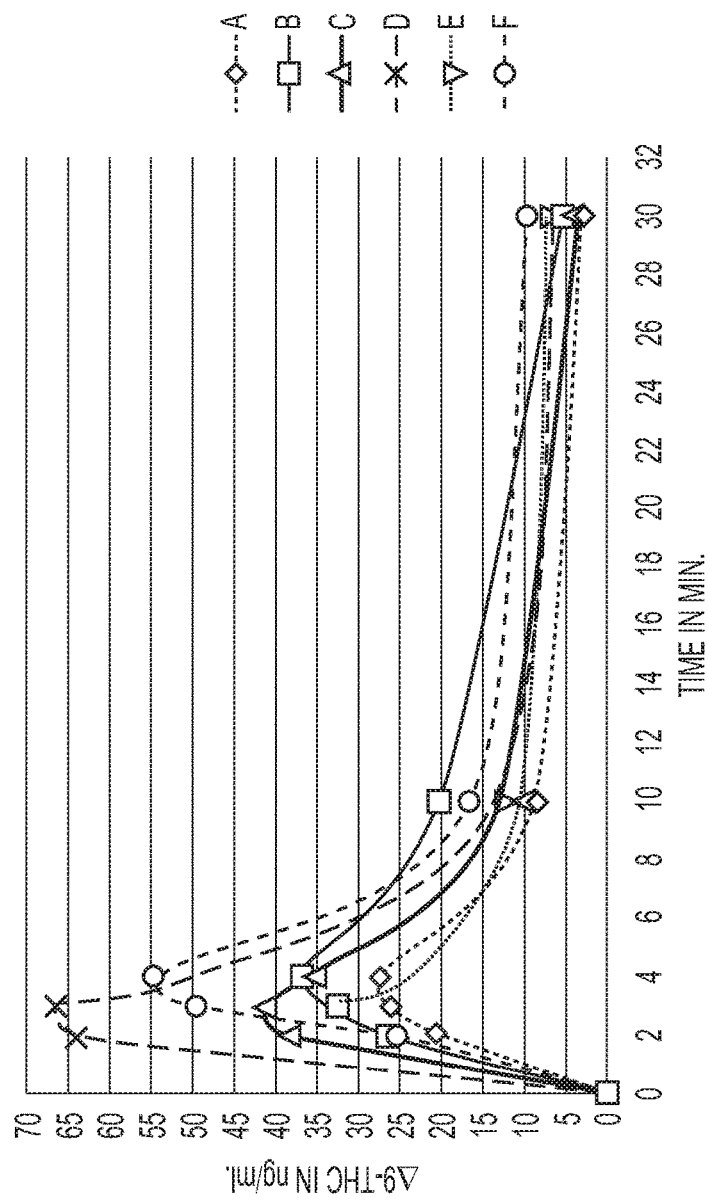
FIG. 14 is a graph of the dose-related (10 mg, 15 mg) inter-individual variability of $\Delta^9$-THC during the absorption phase, in accordance with an example embodiment.
Figure 15:
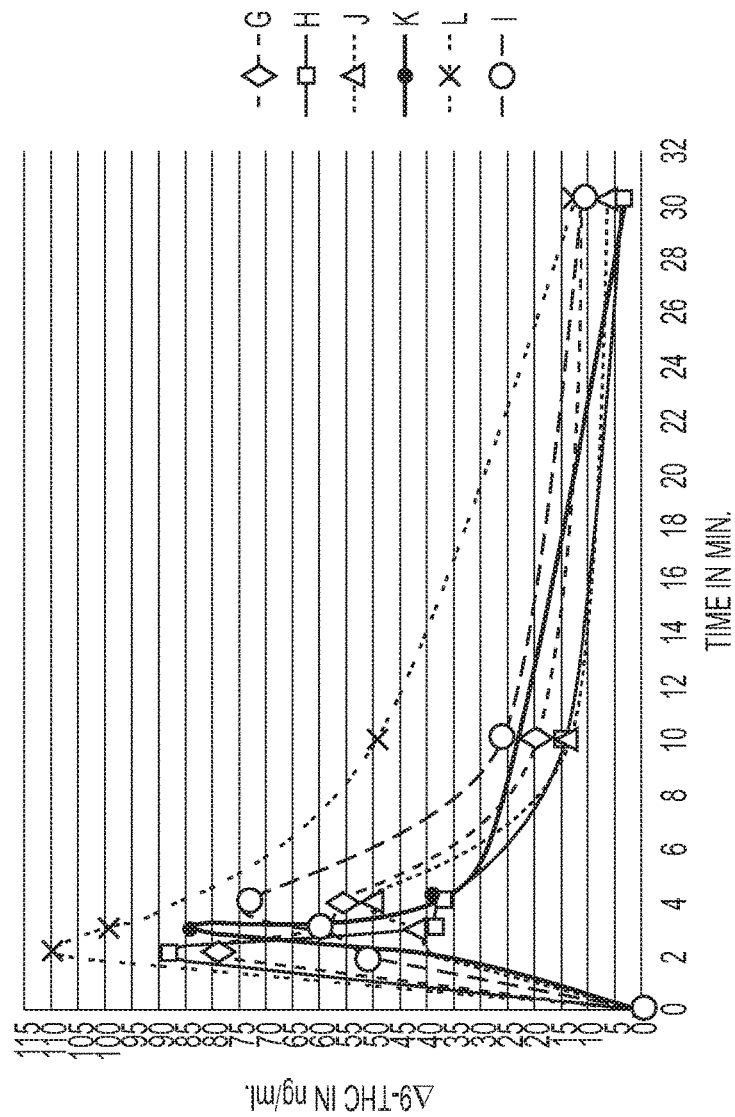
FIG. 15 is a graph of the dose-related (20 mg, 25 mg) inter-individual variability of $\Delta^9$-THC during the absorption phase, in accordance with an example embodiment.

THC $C_{max}$ = tetrahydrocannabinol maximum concentration,
AUC = area under the curve,
$T_{max}$ = time to reach maximum concentration FIGS. 14 and 15 show a graphic delineation of the inter-individual variability of $\Delta^9$-THC during the absorption phase accompanied by each patient's values.

During the time frame of the study no significant change in blood pressure, heart rate, or blood oxygen saturation was observed. Table 3 depicts mean values for each dose group.

TABLE 3

Mean values of systolic and diastolic blood pressure, heart rate and oxygen saturation

| | 10 mg | 15 mg | 20 mg | 25 mg |
|---|---|---|---|---|
| SBP (mmHg) | 113.4 ± 10.23 | 114.93 ± 6.88 | 120.14 ± 28.03 | 130 ± 16.62 |
| DBP (mmHg) | 69.46 ± 7.86 | 63.85 ± 9.78 | 71.78 ± 14.95 | 80.57 ± 8.92 |
| HR | 71.66 ± 10.14 | 79 ± 13.37 | 68.35 ± 5.83 | 77.57 ± 17.74 |
| $SO_2$ (%) | 99.93 ± 0.25 | 100 | 99.92 ± 0.26 | 99.42 ± 0.9 |

SBP = systolic blood pressure;
DBP = diastolic blood pressure;
HR = heart rate;
$SO_2$ = blood oxygen saturation The Short Blessed Test, a six-item test, was used as a diagnostic tool enabling the cognitive status evaluation of the volunteers. Each item was scored and total scores were calculated on the following cut off points: Normal or minimally impaired: 0-8, Moderately impaired: 9-19, Severely impaired: 20-33. All volunteers described minimal cognitive impairment as shown in Table 4.

TABLE 4

Mean values of dose related Short Blessed Tests

| | 10 mg | 15 mg | 20 mg | 25 mg |
|---|---|---|---|---|
| SBT 0 min | 0.66 ± 0.94 | 0 | 2 ± 1.63 | 2 ± 2.82 |
| SBT 30 min | 2.33 ± 3.29 | 1.33 ± 1.88 | 0.66 ± 0.94 | 0 |
| SBT 120 min | 2.66 ± 0.47 | 3 ± 0.81 | 0.66 ± 0.94 | 0 |

SBT = Short Blessed Test score

The primary outcome of the study was to determine the pharmacokinetics profile of $\Delta^9$-THC inhaled by using the heat metered-dose inhaler in an ascending dose fashion. All volunteers inhaled for 3 seconds ascending doses of THC after a segmented heated evaporation of the flos. THC pulmonary absorption is rapid and has a biphasic decline in blood concentration. In comparison, intravenous THC administration yields the highest concentration in the blood, i.e. $C_{max}$ in ng/mL of $\Delta^9$-THC: 43.8 (Reference 1, below); 32.8 (Reference 2, below); and 23.8 (Reference 3, below).

Figure 16:
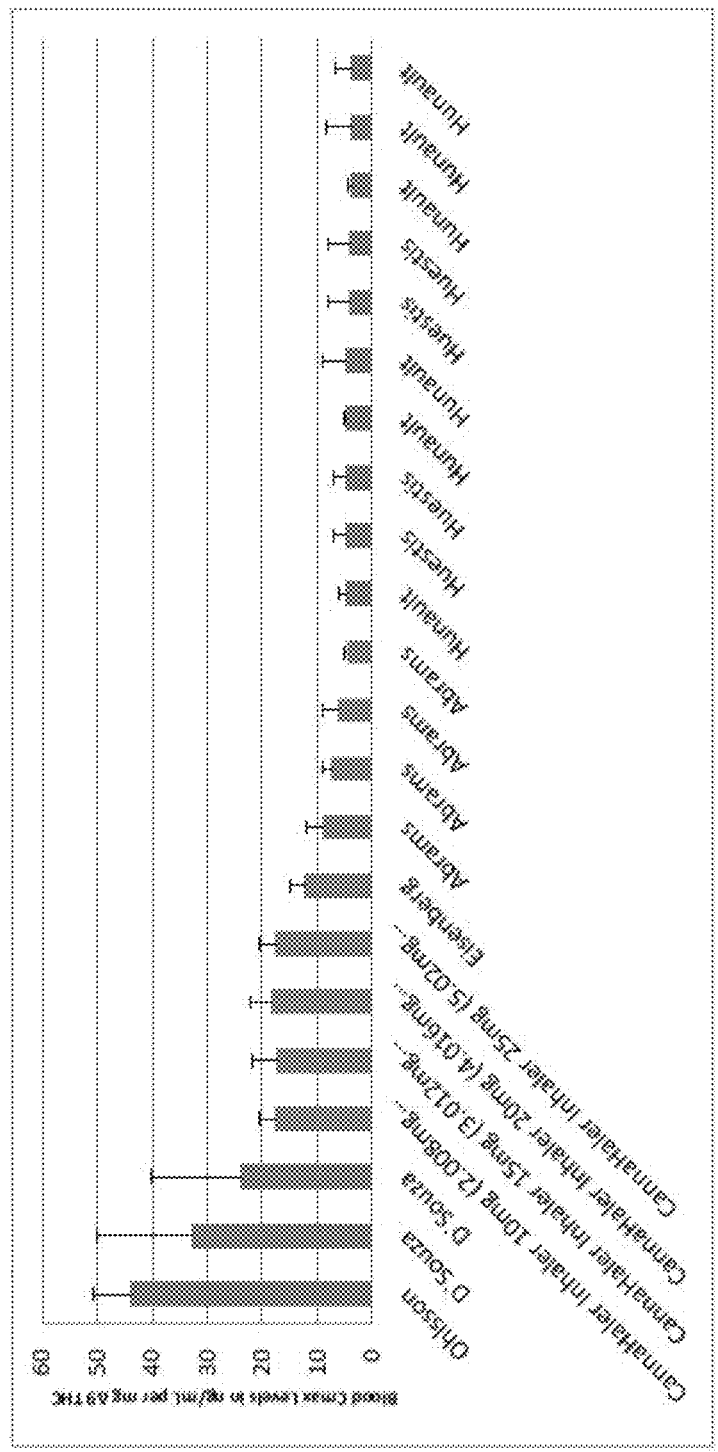
FIG. 16 is a bar chart of plasma $C_{max}$ levels per mg of $\Delta^9$-THC administered, in accordance with an example embodiment.
Figure 17:
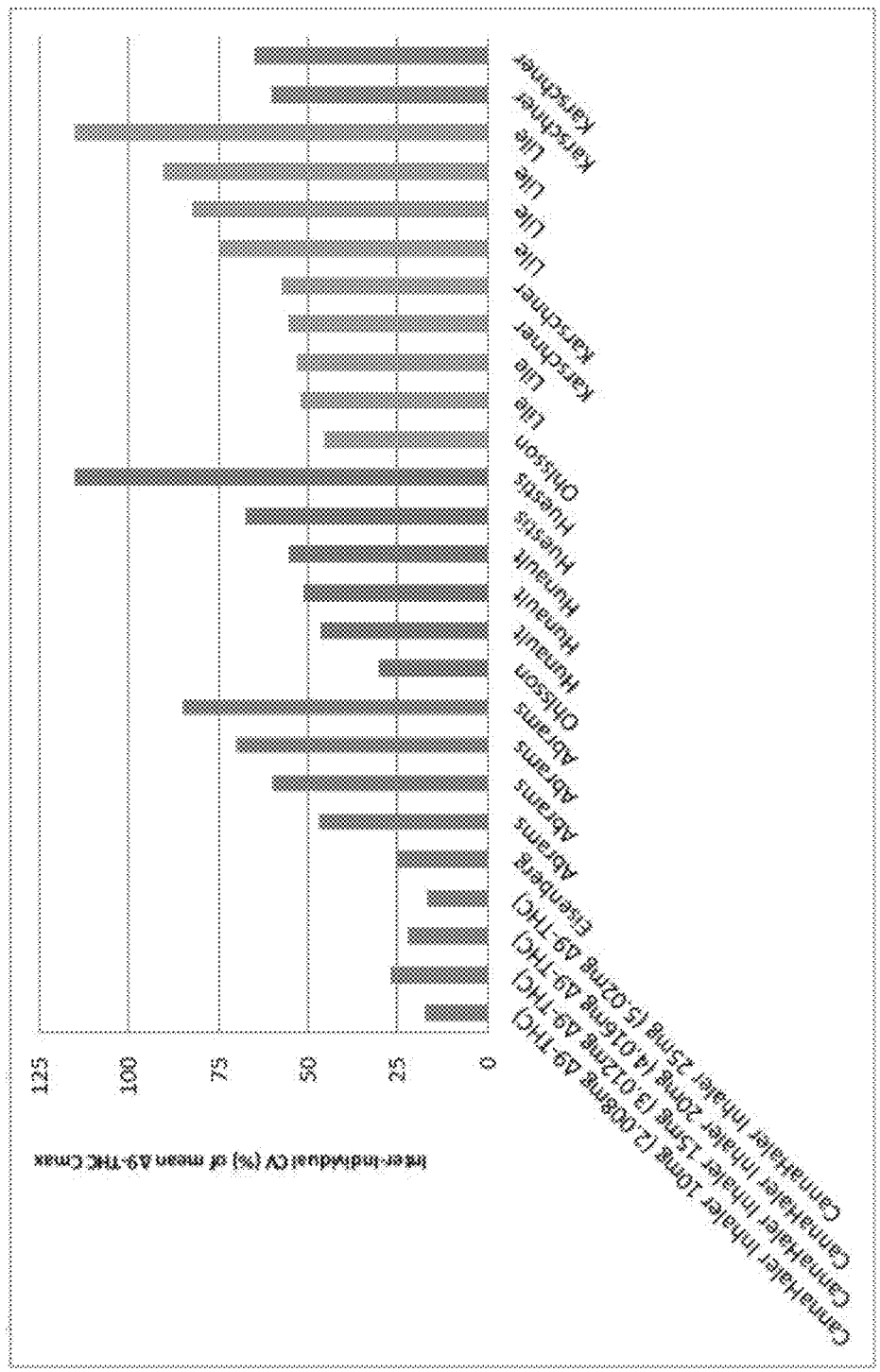
FIG. 17. Is a bar chart of the coefficient of variation CV (%) of different administration modalities, in accordance with an example embodiment.

Various types of pulmonary delivery methods yielded different $C_{max}$ per mg of THC. FIG. 17 compares the results of the inhaler with published data in the literature. The inhaler yielded the highest increase of THC $C_{MAX}$ (17-18 ng/mL/mg) even when compared with the recently published data of the Syqe Inhaler (12.3 ng/mL/mg, Reference 3, below), the Volcano vaporizer (3.9-9 ng/mL/mg, References 4 and 5, below) and smoked *cannabis* (2.9-4.6 ng/mL/mg) (References 4, 7, and 8, below). $C_{max}$ results using the inhaler of the present technology were higher by a factor of 3.9-5.8 compared with smoked *cannabis* (References 8 and 12) and 1.3-1.46 compared with the Syqe inhaler (Reference 3, below). This is most probably because of the longer inhalation when compared to smoked *cannabis* and the transformation to THC from THCA compared to the Syqe inhaler. Because of the inhaler's temperature sensor and its effective feedback and thermal control algorithm a low coefficient of variances was achieved (CV). Literature CV values reported 32%-116% for smoked *cannabis* (References 6, 7, and 8, below), 47%-85% for the vaporizer (References 4 and 9, below) 42%-115% for oral consumption (References 6, 10, and 11, below), and 59%-67% for oro-mucosal administration (Reference 10 below and FIG. 16). The use of the inhaler showed minimal to no adverse effects, all were reversible and rapidly faded. Cognitive tests performed showed normal to minimally impaired cognitive status.

REFERENCES

1. Ohlsson A, Lindgren J E, Wahlen A, et al. Plasma delta-9 tetrahydrocannabinol concentrations and clinical effects after oral and intravenous administration and smoking. Clin. Pharmacol. Ther. 1980; 28:409-416.
2. D'Souza D C, Perry E, MacDougall L, et al. The psychotomimetic effects of intravenous delta-9-tetrahydrocannabinol in healthy individuals: implications for psychosis. Neuropsychopharmacology. 2004; 29:1558-1572.
3. Eisenberg E, Oginz M, Almog S, et al. The pharmacokinetics, efficacy, safety, and ease of use of novel portable metered-dose *cannabis* inhaler in patients with chronic neuropathic pain: a phase 1a study. Journal of Pain & Palliative Care Pharmacotherapy. 2014; 28:216-225.
4. Abrams D I, Vizoso H P, Shade S B, et al. Vaporization as a smokeless *cannabis* delivery system: a pilot study. Clin. Pharmacol. Ther. 2007; 82:572-578.
5. Abrams D I, Couey P, Shade S B, Kelly M E, Benowitz N L. Cannabinoids-opioid interaction in chronic pain. Clin. Pharmacol. Ther. 2011; 90:844-851.
6. Abrams D I, Vizoso H P, Shade S B, et al. Vaporization as a smokeless *cannabis* delivery system: a pilot study. Clin. Pharmacol. Ther. 2007; 82:572-578.
7. Hunault C C, Mensinga T T, de Vries I, et al. Delta-9-tetrahydrocannabinol (THC) serum concentrations and pharmacological effects in males after smoking a combination of tobacco and *cannabis* containing up to 69 mg THC. Psychopharmacology (Berl). 2008; 201:171-181.
8. Hunault C C, van Eijkeren J C, Mensinga T T, et al. Disposition of smoked *cannabis* with high $\Delta^9$-tetrahydrocannabinol content: a kinetic model. Toxicol. Appl. Pharmacol. 2010; 246:148-153.
9. Abrams D I, Couey P, Shade S B, Kelly M E, Benowitz N L. Cannabinoids-opioid interaction in chronic pain. Clin. Pharmacol. Ther. 2011; 90:844-851.
10. Karschner E L, Darwin W D, Goodwin R S, Wright S, Huestis M A. Plasma cannabinoid pharmacokinetics following controlled oral $\Delta^9$-tetrahydrocannabinol and oro-mucosal *cannabis* extract administration. Clin. Chem. 2011; 57:66-75.
11. Lile J A, Kelly T H, Charnigo R J, Stinchcomb A L, Hays L R. Pharmacokinetic and pharmacodynamic profile of superatherapeutic oral doses of $\Delta^9$-tetrahydrocannabinol in *cannabis* subjects. J. Clin. Pharmacol. 2013; 53:680-690.
12. Huestis M A, Sampson A H, Holicky B J, Henningfield J E, Cone E J. Characterization of the absorption phase of marijuana smoking. Clin. Pharmacol. Ther. 1992; 52:31-41.

It will be appreciated by persons of ordinary skill in the art that example embodiments of the present disclosure are not limited to what has been particularly shown and described hereinabove. Rather, the scope of the present disclosure includes both combinations and subcombinations of the various features described hereinabove, as well as variations and modifications thereof that are not in the prior art, which would occur to persons of ordinary skill in the art upon reading the foregoing description. For example, as will be appreciated the control methods discussed above with respect to FIG. 10, 11, 12A or 12B, etc. may be combined and/or run in parallel.

The invention claimed is:

1. A method of producing a plant material vapor, comprising:
    inserting a capsule into a vaporizing unit, the capsule containing a plant material and an internal heater, the vaporizing unit defining a side opening such that the inserting of the capsule is from an exterior of the vaporizing unit to an interior of the vaporizing unit via the side opening; and
    supplying an electric current to the internal heater to heat the plant material within the capsule to generate the plant material vapor.
2. The method of claim 1, wherein the inserting includes the capsule being positioned completely within the interior of the vaporizing unit.
3. The method of claim 1, wherein the capsule includes at least a first cover and a second cover.
4. The method of claim 3, wherein the plant material and the internal heater are between the first cover and the second cover.
5. The method of claim 3, wherein the capsule further includes a central housing portion between the first cover and the second cover.
6. The method of claim 3, wherein the first cover defines first perforations and the second cover defines second perforations.
7. The method of claim 6, wherein the inserting includes the capsule being oriented to facilitate an ingress of air via one of the first perforations and the second perforations and an egress of the plant material vapor via the other of the first perforations and the second perforations.
8. The method of claim 1, wherein the plant material is tobacco.
9. The method of claim 1, wherein the internal heater has a planar form.
10. The method of claim 1, wherein the supplying of the electric current results in a resistive heating of the plant material.
11. The method of claim 1, wherein the supplying of the electric current is through an underside of the capsule.
12. The method of claim 11, wherein the vaporizing unit includes a pair of electrodes configured to electrically engage the underside of the capsule.
13. The method of claim 1, further comprising:
    supplying a preliminary current to the internal heater to preheat the plant material prior to the supplying of the electric current to the internal heater to heat the plant material to generate the plant material vapor.

* * * * *